United States Patent
Fleming et al.

(10) Patent No.: US 11,207,480 B2
(45) Date of Patent: *Dec. 28, 2021

(54) INDUCTION MOTOR CONTROL

(71) Applicant: RESMED MOTOR TECHNOLOGIES INC., Chatsworth, CA (US)

(72) Inventors: David James Fleming, Cardiff, CA (US); Michael Grunberg, Canoga Park, CA (US); Aleksandr S. Nagorny, Canoga Park, CA (US); Siavash Sadeghi, Northridge, CA (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,469

(22) Filed: Mar. 20, 2020

(65) Prior Publication Data

US 2020/0215282 A1  Jul. 9, 2020

Related U.S. Application Data

(63) Continuation of application No. 15/502,581, filed as application No. PCT/US2015/050429 on Sep. 16, 2015, now Pat. No. 10,625,035.

(Continued)

(51) Int. Cl.
*A61M 16/00* (2006.01)
*H02P 23/08* (2006.01)
(Continued)

(52) U.S. Cl.
CPC .... *A61M 16/0066* (2013.01); *A61M 16/0069* (2014.02); *A61M 16/024* (2017.08);
(Continued)

(58) Field of Classification Search
CPC .......... A61M 16/0069; A61M 16/0066; A61M 2205/42; A61M 16/024; A61M 16/16;
(Continued)

(56) References Cited

U.S. PATENT DOCUMENTS

| | | |
|---|---|---|
| 5,269,660 A | 12/1993 | Pradelle |
| 6,353,302 B1 | 3/2002 | Ramachandran et al. |

(Continued)

OTHER PUBLICATIONS

Extended European Search Report and Written Opinion for EP15842310.3 dated Feb. 20, 2018.

(Continued)

*Primary Examiner* — Peter J Bertheaud
(74) *Attorney, Agent, or Firm* — Botos Churchill IP Law LLP

(57) ABSTRACT

A method of a control system controls an inductance motor in a device that may include an impeller using a pressure compensation control system. The control system may be implemented in a respiratory pressure therapy device. The control system may include a sensor configured to provide a pressure signal indicative of the pressure of a flow of fluid produced by the device. A measured pressure may be compared to a set pressure to determine a pressure error. A slip frequency may be adjusted as a function of the pressure error in an attempt to eliminate or minimise the pressure error.

28 Claims, 14 Drawing Sheets

Related U.S. Application Data

(60) Provisional application No. 62/135,880, filed on Mar. 20, 2015, provisional application No. 62/052,020, filed on Sep. 18, 2014.

(51) Int. Cl.
| | |
|---|---|
| *A61M 16/10* | (2006.01) |
| *F04D 27/00* | (2006.01) |
| *F04D 29/28* | (2006.01) |
| *A61M 16/16* | (2006.01) |
| *F04D 17/16* | (2006.01) |
| *F04D 25/06* | (2006.01) |

(52) U.S. Cl.
CPC ........... *A61M 16/10* (2013.01); *F04D 27/004* (2013.01); *F04D 29/281* (2013.01); *H02P 23/08* (2013.01); *A61M 16/0051* (2013.01); *A61M 16/026* (2017.08); *A61M 16/16* (2013.01); *A61M 2016/0027* (2013.01); *A61M 2016/0039* (2013.01); *A61M 2205/3368* (2013.01); *A61M 2205/42* (2013.01); *A61M 2205/581* (2013.01); *A61M 2205/582* (2013.01); *A61M 2205/583* (2013.01); *F04D 17/16* (2013.01); *F04D 25/06* (2013.01); *F05D 2270/301* (2013.01)

(58) Field of Classification Search
CPC .... A61M 16/10; F04D 29/281; F04D 27/004; H02P 23/08
See application file for complete search history.

(56) References Cited

U.S. PATENT DOCUMENTS

| | | |
|---|---|---|
| 6,637,433 B2 | 10/2003 | Schoeb |
| 7,539,549 B1 | 5/2009 | Discenzo et al. |
| 8,356,983 B2 | 1/2013 | Shizuo et al. |
| 10,625,035 B2 * | 4/2020 | Fleming ................ F04D 27/004 |
| 2008/0260541 A1 | 10/2008 | Lifson et al. |
| 2009/0097988 A1 | 4/2009 | Shizuo et al. |
| 2014/0158131 A1 | 6/2014 | Kenyon et al. |
| 2014/0167658 A1 | 6/2014 | Kwon et al. |

OTHER PUBLICATIONS

International Search Report and Written Opinion for Application No. PCT/US15/50429 dated Dec. 30, 2015.

\* cited by examiner

INDUCTION MOTOR CONTROL

1 CROSS-REFERENCE TO RELATED APPLICATIONS

This application is a continuation of U.S. patent application Ser. No. 15/502,581 filed on Feb. 8, 2017 which is a national phase entry under 35 U.S.C. § 371 of International Application No. PCT/US2015/50429 filed Sep. 16, 2015, published in English, which claims priority from U.S. Provisional Patent Application No. 62/135,880 filed on Mar. 20, 2015 and U.S. Provisional Patent Application No. 62/052,020 filed Sep. 18, 2014, and, all of which are incorporated herein by reference.

2 BACKGROUND OF THE INVENTION

2.1 Field of the Invention

The present technology relates to electronically commutated motors, particularly Alternating Current (AC) induction motors, and the use thereof. These types of electronically commutated motors produce continuous rotational torque without the use of permanent magnets. The present technology further relates to a control algorithm for a blower comprising an induction motor. In some aspects the motors may be used in medical devices or apparatus configured to treat, prevent and/or ameliorate respiratory-related disorders.

2.2 Description of the Related Art

2.2.1 Electrical Motors

One of the subgroups of electrical motors are brushless D.C. motors. Brushless D.C. motors are well known and used in a range of devices. Brushless D.C. motors typically include permanent magnets coupled to or on a rotor and windings formed on a laminated stator that form electromagnets when current is applied to the stator. High energy permanent magnets used in motors may be made from materials which include rare earth elements such as samarium-cobalt and neodymium-iron-boron. However, such permanent magnets are expensive resulting in a higher cost motor. Furthermore the availability of these rare earth metals is limited. To reduce costs other forms of electrical motors that do not require permanent magnets or windings associated with the rotor were developed.

A common class of electrical motor that do not include permanent magnets are called induction motors. Induction motor is another name of asynchronous motor and may be a single phase induction motor or a three phase induction motor. The most common induction motors are three phase induction motors as this type of motor is capable of self-starting and does not require additional starting features like single phase induction motor. An induction motor does not require a commutator and the electromechanical part of the motor includes two main parts, a stator and a rotor. The stator includes three phase windings wound in stator slots on the stator. Current is supplied to the different phases of the stator windings to generate a rotating magnetic field. The rotor is located within the stator and comprises bars of conducting metal material such as copper or aluminium or some alloys. There is no direct voltage supply provided to the rotor, the rotor is excited by virtue of electromagnetic induction caused by the rotating magnetic field created in the stator windings. Thus, the current in the rotor is induced from the current in the stator windings. The induced current in the rotor causes the rotor to rotate in the same direction as the rotating magnetic field in the stator. However, the rotor does not rotate at the same speed as the rotating magnetic field and the difference in speed between the rotating magnetic field and the rotor speed is called the slip and is given by the ratio:

$$S=(N_s-N)/N_s \quad [1]$$

Where S is the slip, $N_s$ is the synchronous speed in revolutions per minute (RPM), and N is the rotor speed. The Synchronous speed in RPM is given by:

$$Ns=120(f)/P \quad [2]$$

Where f is the supply frequency in Hertz (Hz) and P is the number of poles created by stator winding.

Thus, the rotor current is proportional to the relative speed between the speed of rotating field created by the stator winding and the rotor speed. The rotor current and hence the torque are both directly proportional to the slip. The rotor current is also proportional to the rotor resistance. Increasing the rotor resistance will reduce the current and increase the slip; hence a form of speed and torque control is possible with wound rotor motors.

Consequently generally induction motors have been controlled by measuring the speed of the rotor with a speed measurement device such as a tachometer, encoder, resolver or hall sensors. As the actual speed of the rotor is different from the synchronous speed or frequency of the rotating stator magnetic field, the speed of the rotor needs to be measured to determine the slip speed or slip frequency. The speed of an induction motor is controlled by varying the frequency and supply voltage of the power supplied to the motor stator using a Volts/Hertz controller. FIG. 1 shows a prior art control system for an induction motor that requires the speed of the rotor to be measured by a speed sensor or tachometer.

There is a relationship between motor flux and the supplied voltage and frequency as defined by the following equation:

$$B=KV/f \quad [3]$$

Where B is the flux density, V is the supplied voltage, f is the supply frequency and K is a constant depending on the shape and configuration of the stator poles.

Therefore increasing the frequency without increasing the voltage will cause a reduction of the flux in the magnetic circuit thus reducing the motor's output torque. The reduced motor torque will tend to increase the slip with respect to the new supply frequency. This in turn causes a greater current to flow in the stator, increasing the IR (current (I)*resistance (R)) voltage drop across the windings as well as the $I^2R$ power losses in the windings. The result is a major drop in the motor efficiency. Increasing the frequency still further will ultimately cause the motor to stall.

Induction motors are commonly used in constant speed devices whose speed is proportional to the mains frequency provided. However, variable speed induction motors are available but require a motor controller that provides a variable frequency and voltage output and this increases the size and cost of the motor drive. Induction motors have been used in a range of heavy industry applications, machine tools and domestic appliances such as washing machines, pumps, lifts, cranes, large capacity exhaust fans and mills. Generally induction motors are relatively large and are rarely used in small power ranges and high speed devices especially medical devices due to lower efficiency and manufacturing challenges.

There is further need to reduce one or more of the cost, reliability, control and/or size of induction motors if they are to be used in medical devices.

2.2.2 Motor Applications

Motors are used to drive a variety of devices in a diverse range of applications including but not limited to fans, pumps, medical devices, automotive industry, aerospace, toys, power tools, disk drives, and household appliances. Motors have been used in medical devices to generate a supply of pressurized gas for example in Respiratory Pressure Therapy (RPT) Devices including Positive Airway Pressure (PAP) devices and ventilators. These RPT devices generally include permanent magnet brushless D.C. motors. Induction motors generally have not been used in such RPT devices due to their generally larger size and the cost of control.

The noise produced by some medical devices is required to be relatively low so as not to disturb the user. In particular for medical devices that may be used for long periods of time, such as throughout the day, and/or during sleep, such as PAP devices and/or ventilators the level of noise emitted is a significant issue. Sound pressure values of a variety of objects are listed below:

| Object | A-weighted sound pressure dB(A) | Notes |
| --- | --- | --- |
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| ResMed S9 AutoSet ™ PAP device | 26.5 | |
| Background in TV studio | 20 | |

2.2.3 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

2.2.4 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). As a result, a medical humidifier may be small for bedside placement, and may be configured to only humidify and/or heat the flow of air delivered to the patient without humidifying and/or heating the patient's surroundings. Room-based systems (e.g. a sauna, an air conditioner, or an evaporative cooler), for example, may also humidify air that is inspired by the patient, however those systems would also humidify and/or heat the entire room, which may cause discomfort to the occupants. Furthermore medical humidifiers may have more stringent safety constraints than industrial humidifiers

3 BRIEF SUMMARY OF THE TECHNOLOGY

The present technology is directed towards induction motors and devices that comprise such induction motors.

A first aspect of the present technology relates to a method of controlling an induction motor.

Another aspect of the present technology related to a control system for an induction motor configured to adjust a slip frequency of the induction motor based on a measured characteristic of a flow of fluid produced by a rotating rotor of the induction motor.

Another aspect of the present technology relates to an error compensation control system for an induction motor in a blower such as a pressure error compensator control system.

Another aspect of the present technology relates to a control system for an induction motor in a blower, the blower comprising at least one impeller configured to generate a supply of pressurized fluid, the control system comprising a sensor to provide a signal indicative of a measured of a characteristic of the pressurized fluid generated by the blower and a controller configured to receive the signal and determine the measure of the characteristic of the pressurized fluid being generated. The controller configured to compare the determined measured characteristic with a predetermined level of the characteristic and to adjust a slip frequency of the induction motor as a function of the comparison. The characteristic of the pressurized fluid may be a pressure of the fluid.

Another aspect of the present technology relates to a control system for an induction motor in a blower configured to compare a measured pressure with a set pressure to determine a pressure error and adjust the frequency and voltage supplied to a stator of the induction motor to eliminate or reduce the pressure error. The frequency and voltage supplied to the stator may be determined as a function of a slip frequency.

A further aspect of the present technology relates to a blower including an induction motor.

A still further aspect relates to a respiratory therapy device comprising a blower including an induction motor.

Another aspect of the present technology relates to a method of controlling the rotor speed of an induction motor by determining a slip frequency based on a measured characteristic of a flow of fluid produced by the rotating rotor of the induction motor and adjusting a stator frequency as a function of the determined slip frequency.

A further aspect of the present technology relates to a method of controlling the speed of an induction motor in a blower configured to provide a supply of pressurized fluid, the method comprising setting a desired pressure level of the supply of fluid to be provided by the blower; determining a desired rotor speed based on the set pressure level; determining a slip frequency and stator frequency based on the desired rotor speed; providing excitation to the stator based on the determined stator frequency to induce rotation of the rotor; measuring a pressure of the pressurized supply of fluid generated by the blower; comparing the measured pressure and the set pressure to determine a pressure error; and adjusting the slip frequency based on the determined pressure error to minimise the pressure error and adjust the rotor speed of the blower.

Of course, portions of the aspects may form sub-aspects of the present technology. Also, various ones of the sub-aspects and/or aspects may be combined in various manners and also constitute additional aspects or sub-aspects of the present technology.

Although described in relation to medical devices the induction motor and control system of the present technology may be used in a range of applications.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Motor

4.2 System

Figure 3:
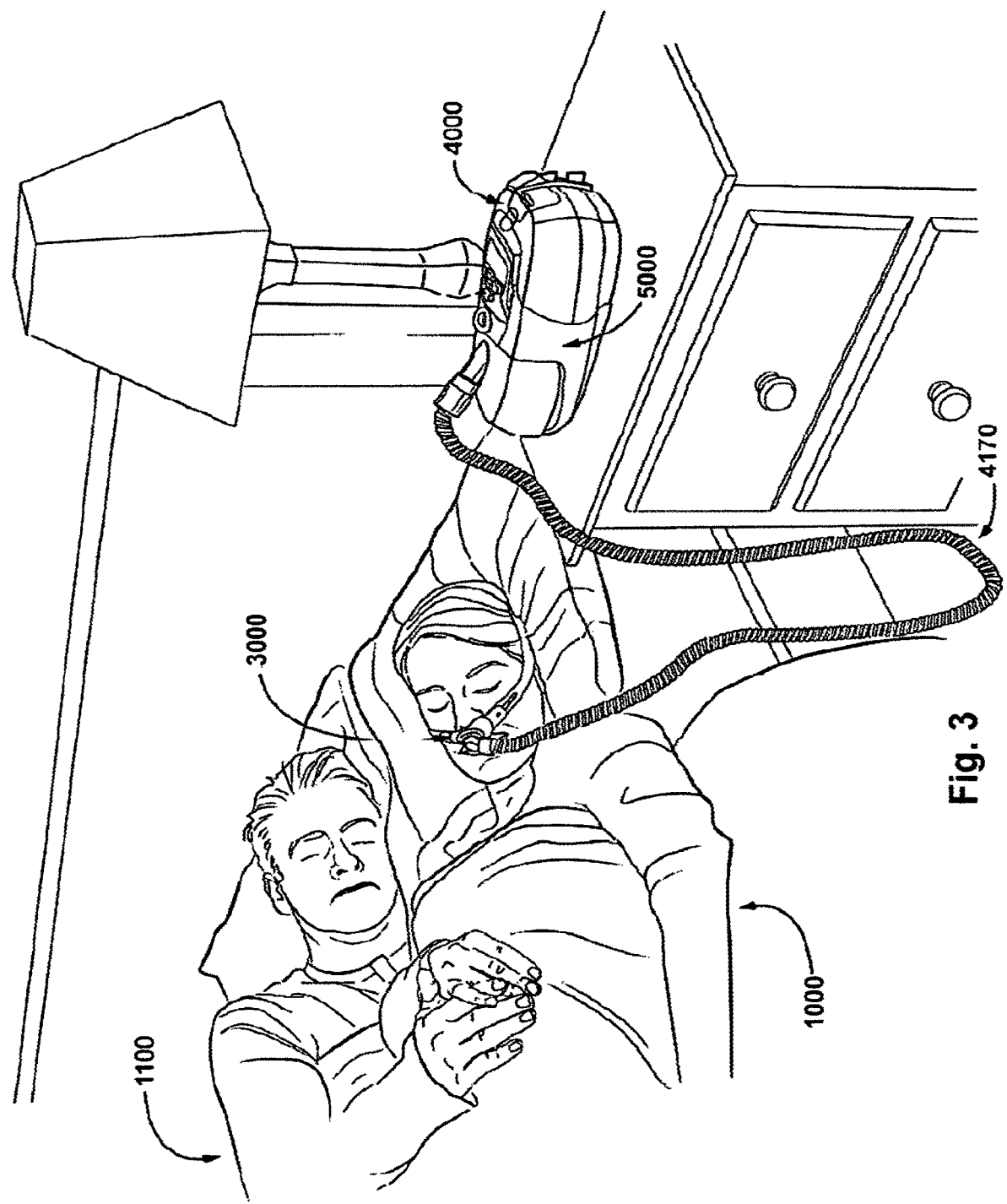

FIG. 3 shows a system in accordance with the present technology. A patient 1000 wearing a patient interface 3000, receives a supply of air at positive pressure from a RPT device 4000. Air from the RPT device is humidified in a humidifier 5000, and passes along an air circuit 4170 to the patient 1000. A bed partner 1100 may also be present when the patient uses the system.

4.3 Pap Device

Figure 4A:
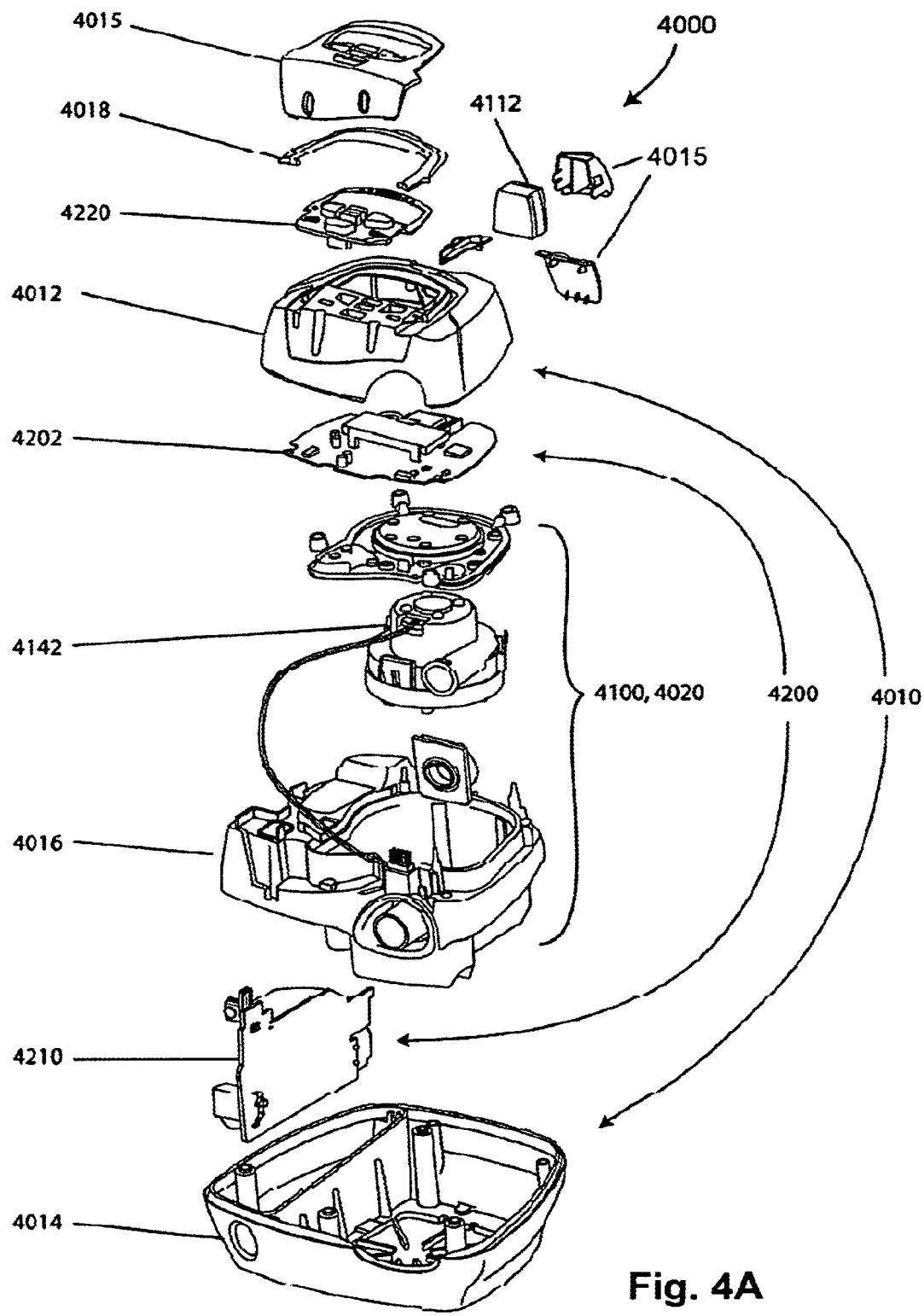

FIG. 4A shows a RPT device in accordance with one form of the present technology.

Figure 4B:
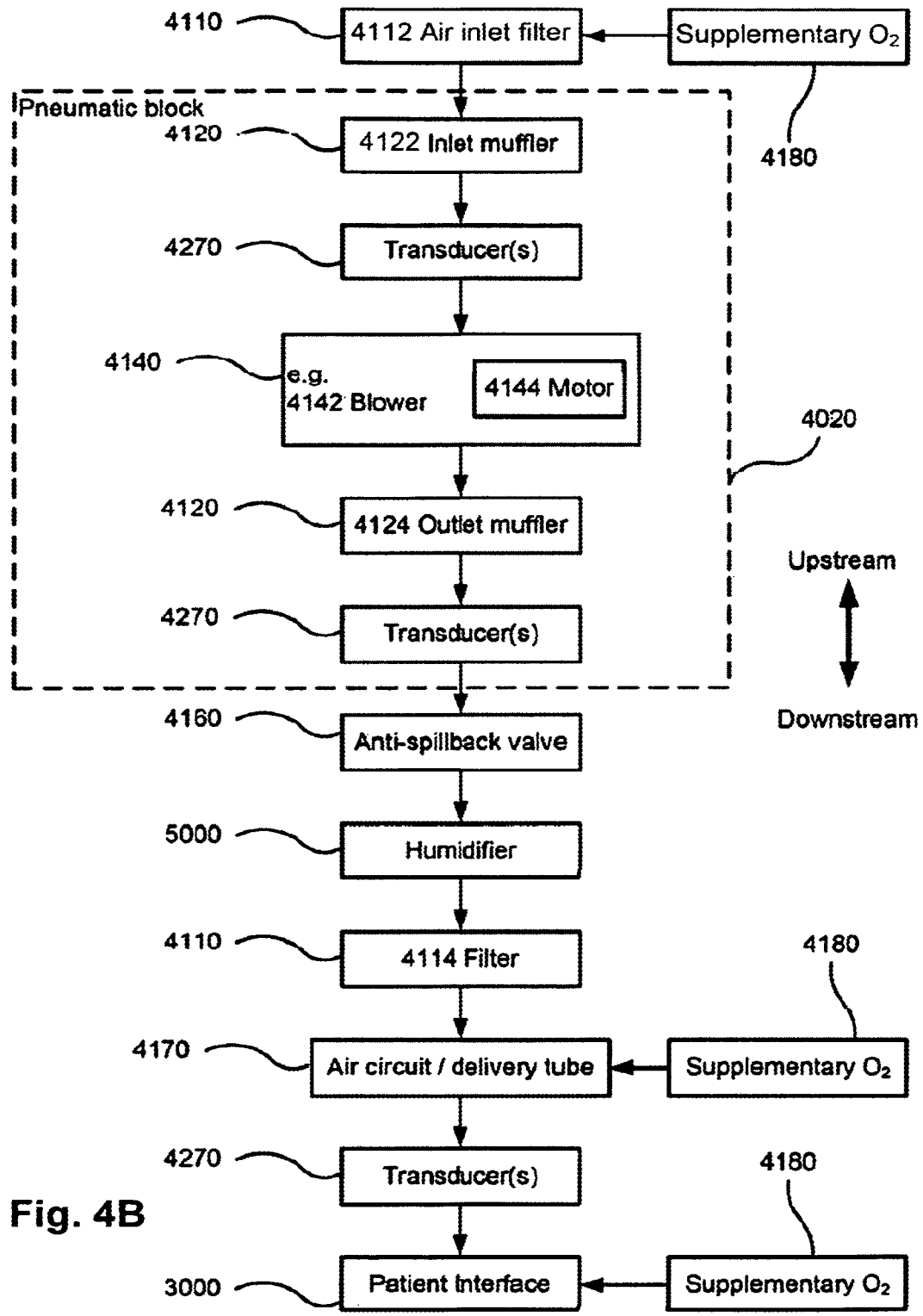

FIG. 4B is a schematic diagram of the pneumatic circuit of a RPT device in accordance with one form of the present technology. The directions of upstream and downstream are indicated.

Figure 4C:
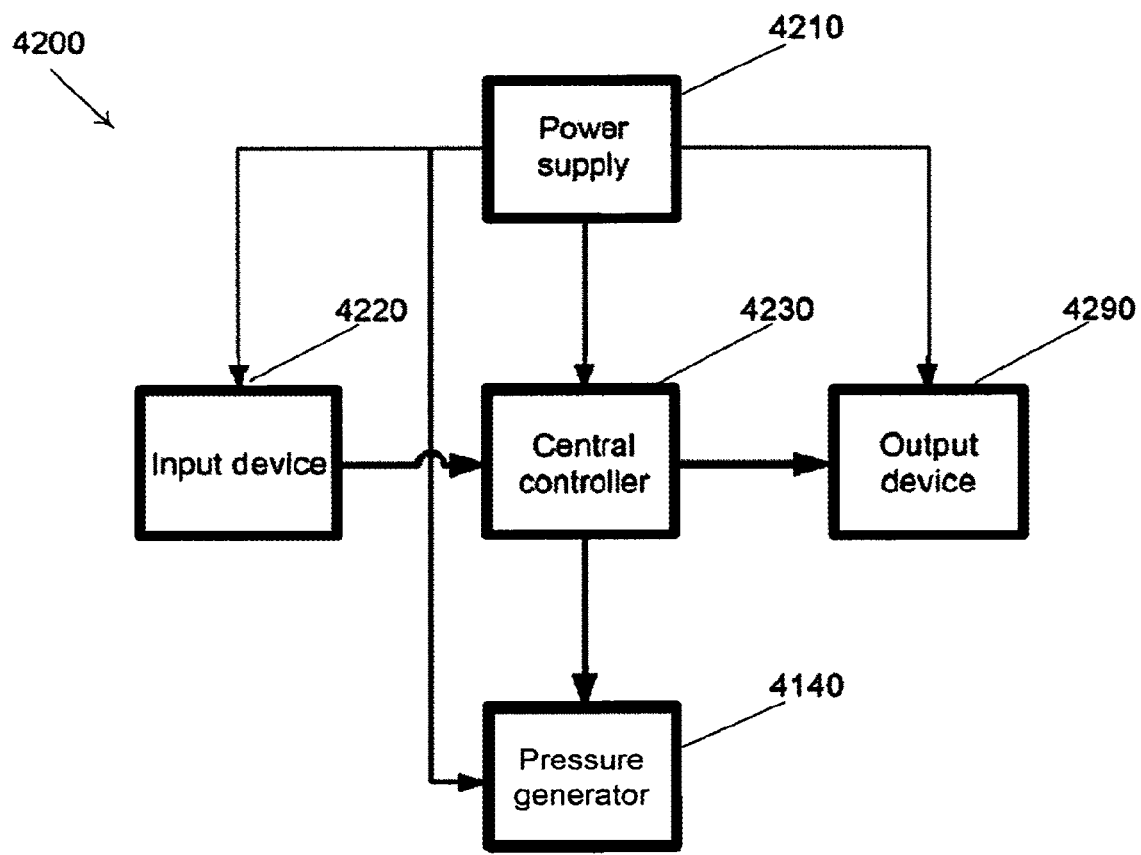

FIG. 4C is a schematic diagram of the electrical components of a RPT device in accordance with one form of the present technology.

Figure 4D:
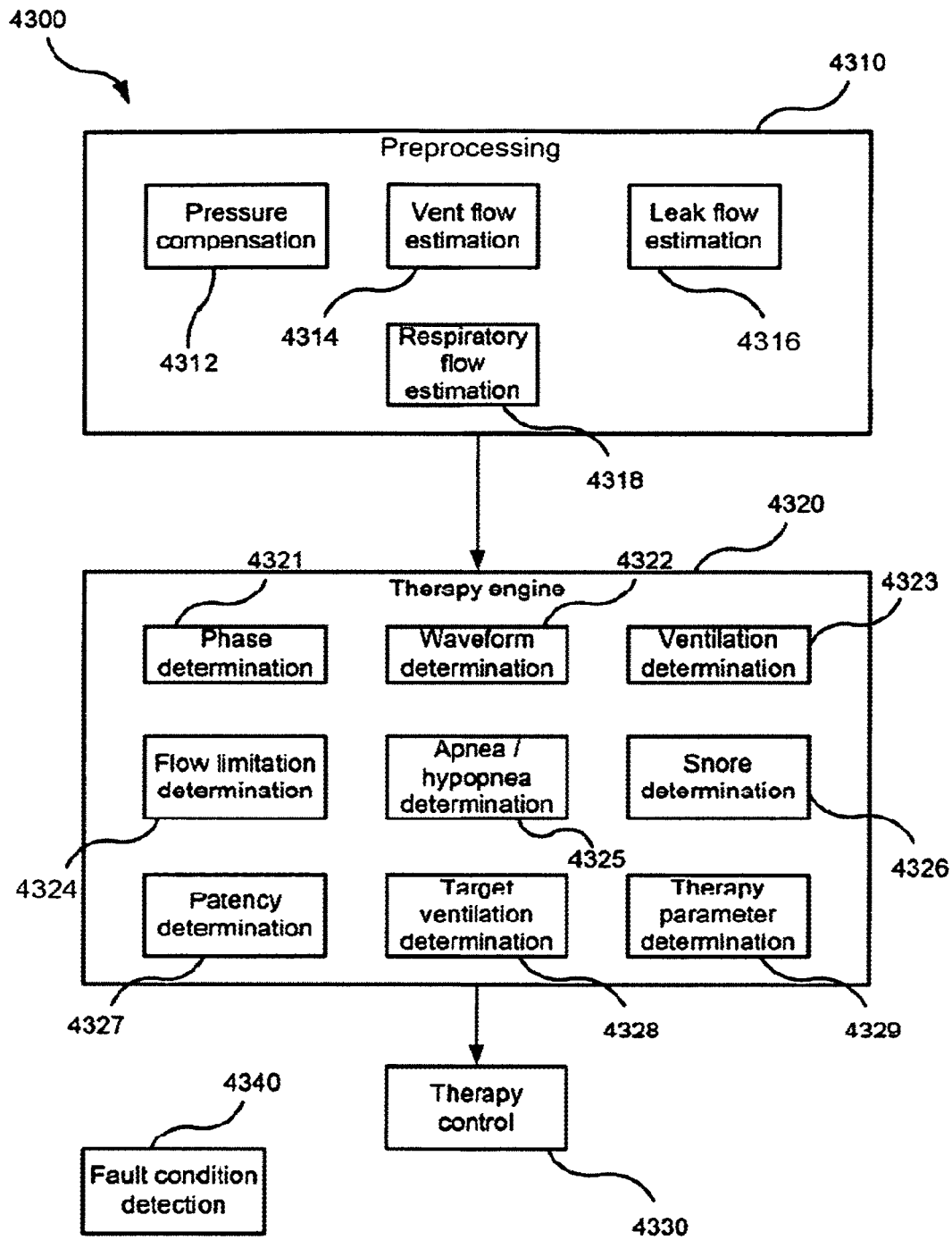

FIG. 4D is a schematic diagram of exemplary algorithms that may be implemented in a RPT device.

4.4 Humidifier

Figure 5A:
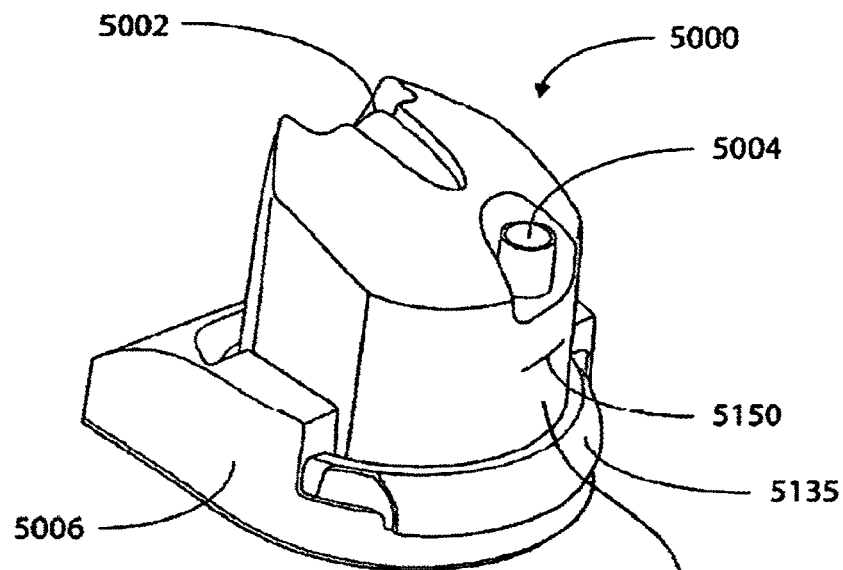

FIG. 5A shows an isometric view of a humidifier in accordance with one form of the present technology.

Figure 5B:
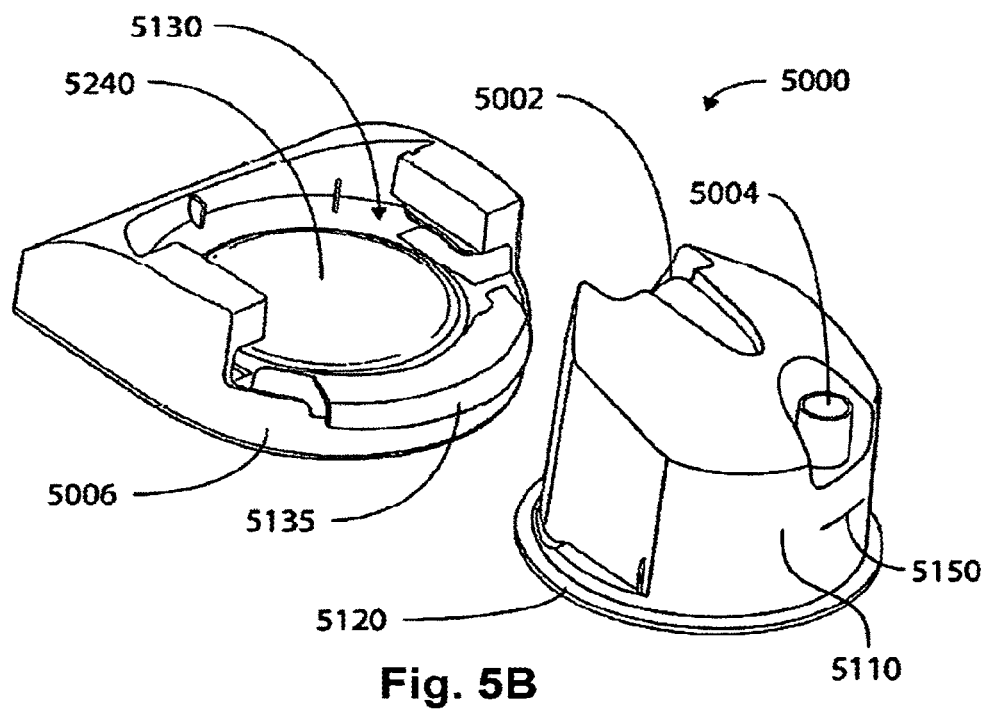

FIG. 5B shows an isometric view of a humidifier in accordance with one form of the present technology, showing a humidifier reservoir 5110 removed from the humidifier reservoir dock 5130.

Figure 5C:
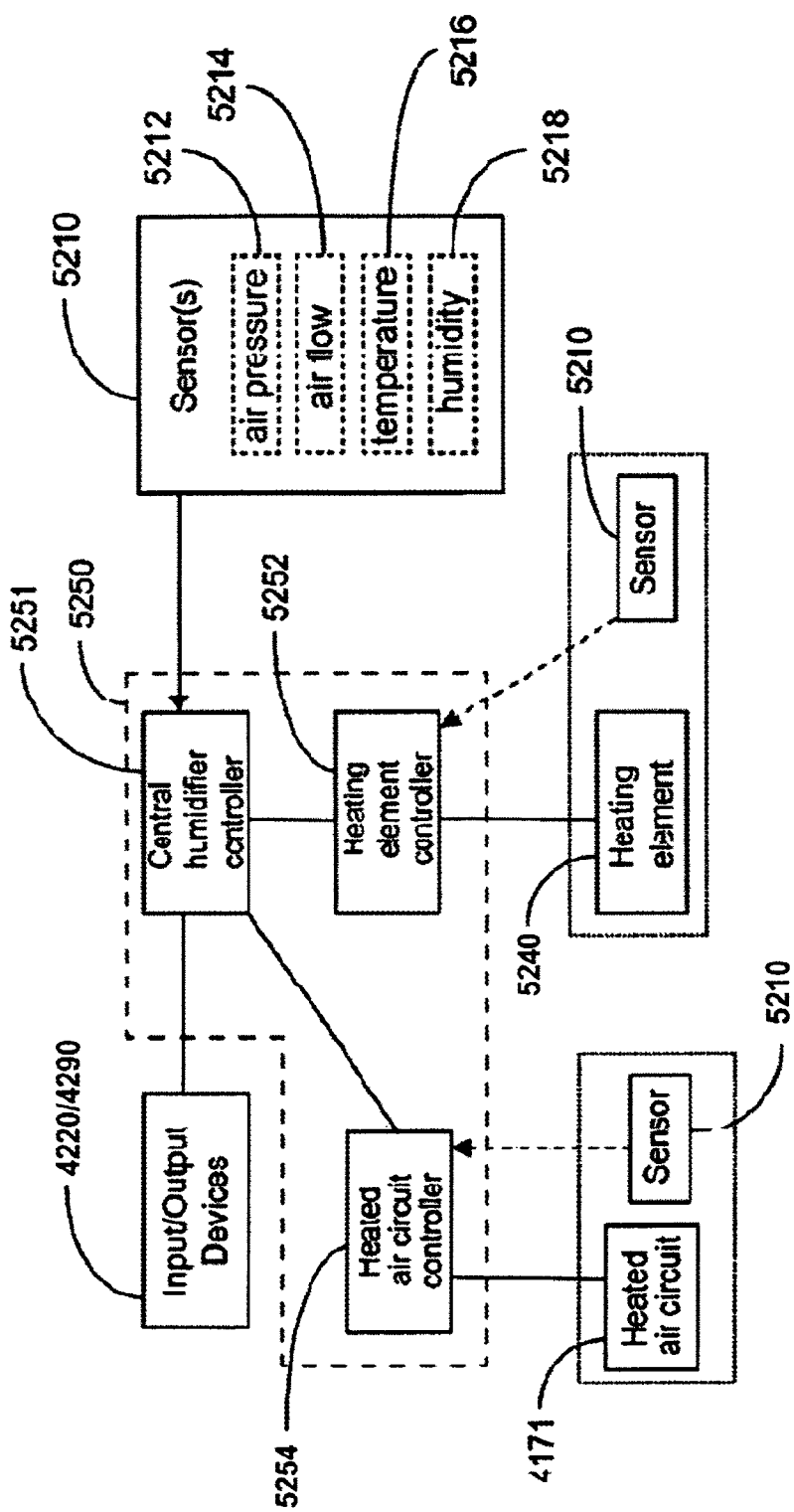

FIG. 5C is a schematic of components of a humidifier in accordance with one form of the present technology.

4.5 Breathing Waveforms

Figure 6A:
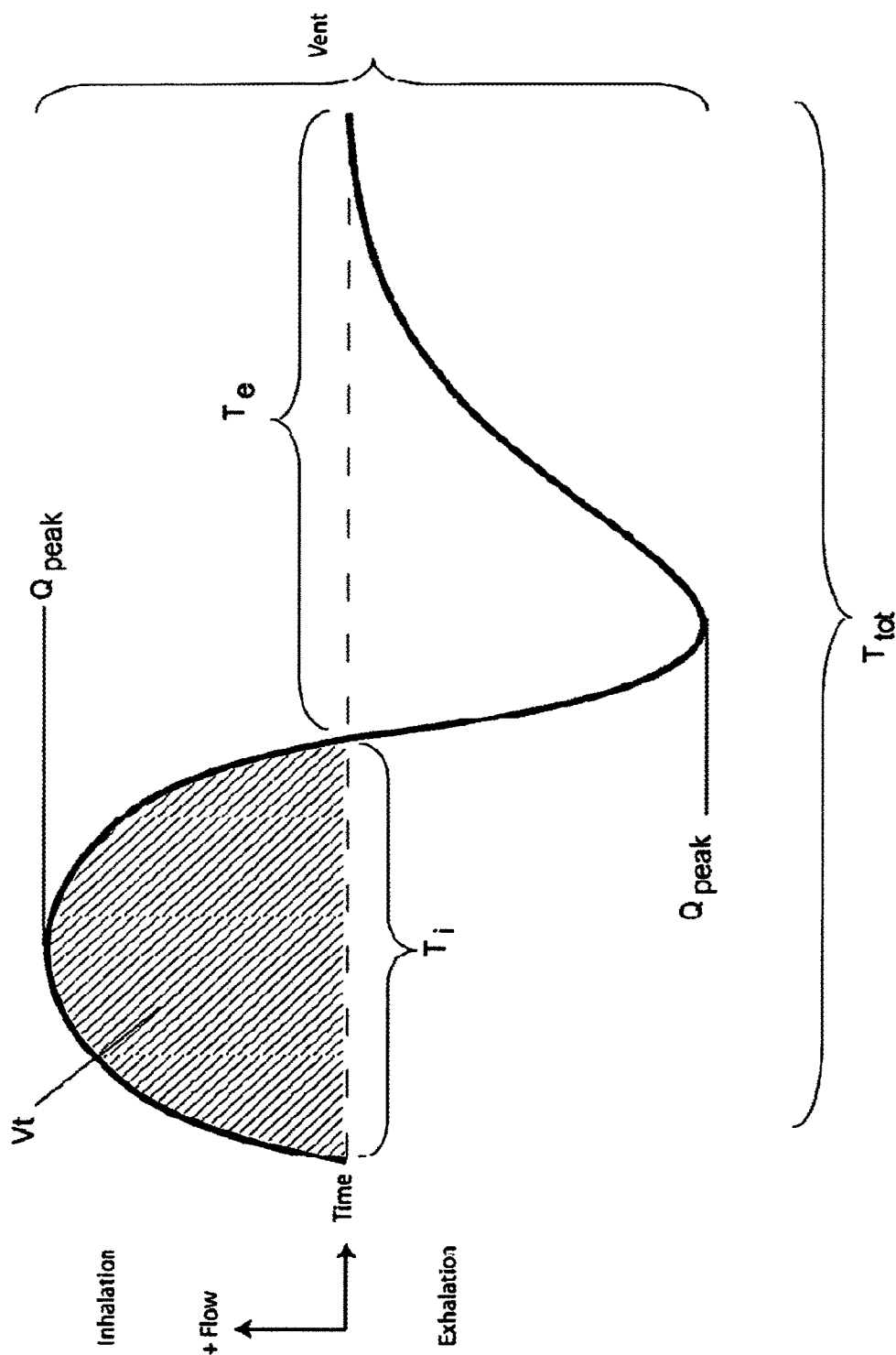

FIG. 6A shows a model typical breath waveform of a person while sleeping.

Figure 6B:
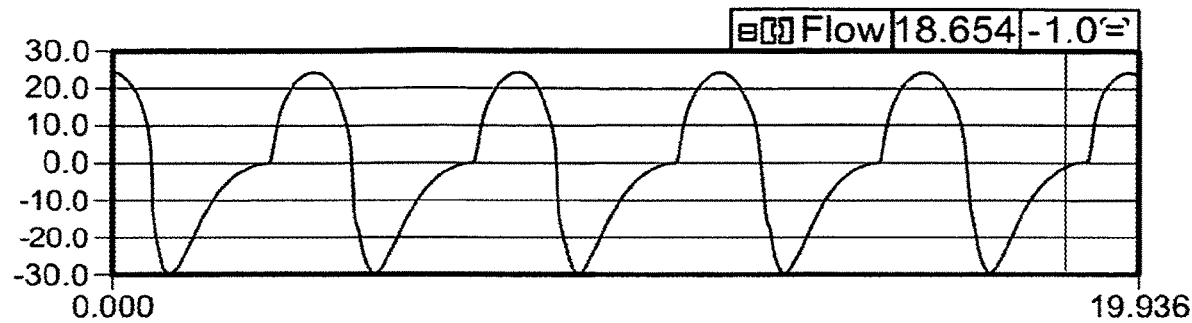

FIG. 6B shows a flow curve for a breathing cycle at a rate of 15 breaths per minutes.

Figure 6C:
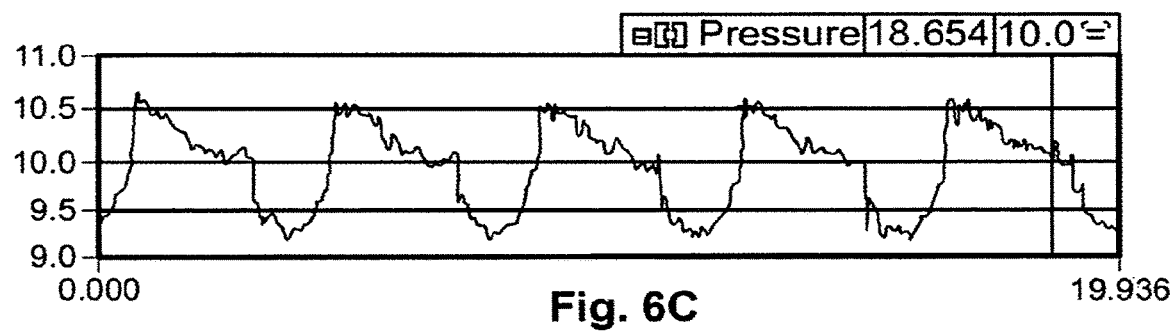

FIG. 6C shows the pressure profile over a plurality of breathing cycles with a set pressure of 10 cmH$_2$O using a blower comprising an induction motor and controlled using the control system of the present technology.

Figure 6D:
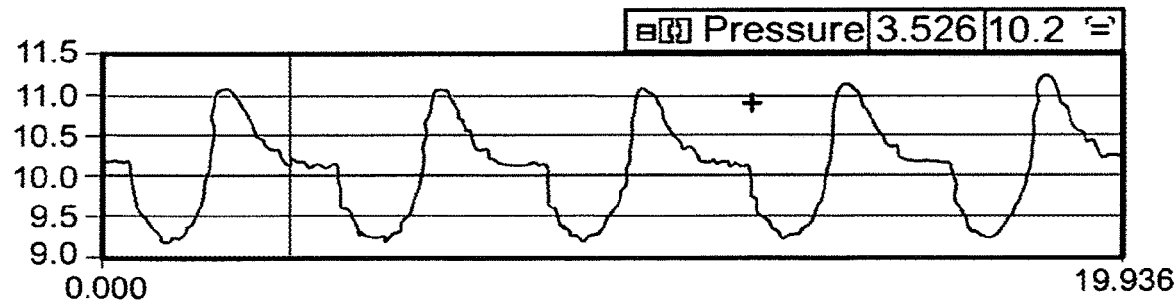

FIG. 6D shows the pressure delivered over a plurality of breathing cycles with a set pressure of 10 cmH$_2$O using a blower of the prior art comprising a Brushless DC motor.

Figure 7A:
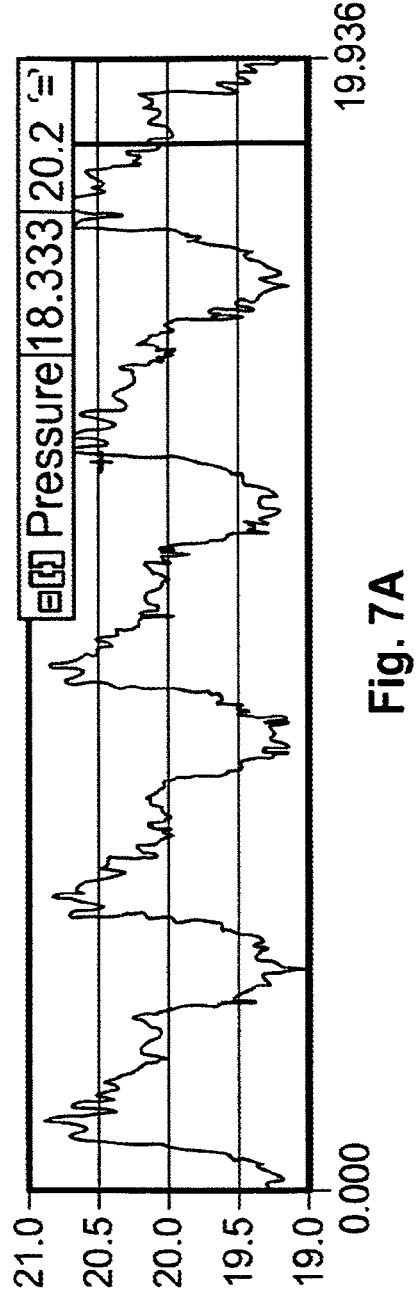

FIG. 7A shows the pressure profile over a plurality of breathing cycles with a set pressure of 20 cmH2O using a blower comprising an induction motor and controlled using the control system of the present technology.

Figure 7B:
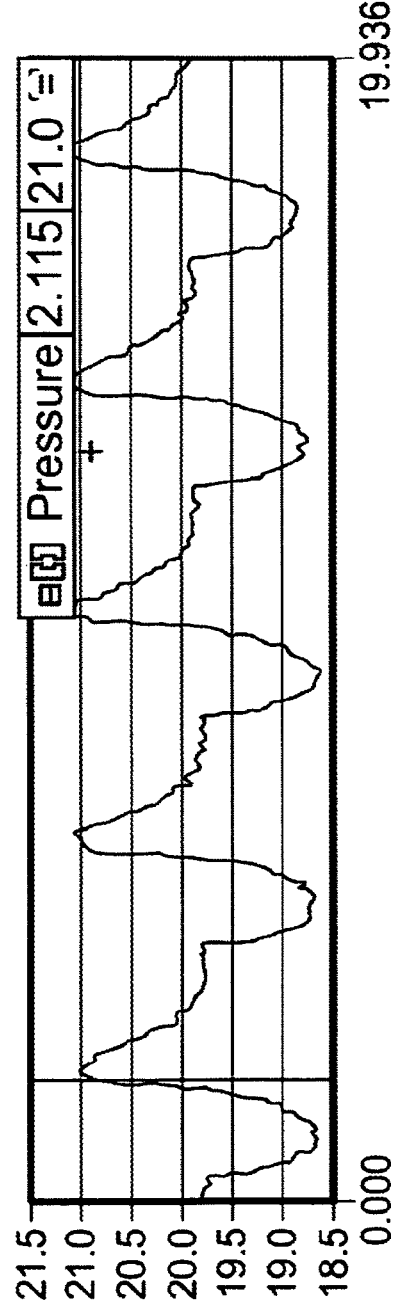

FIG. 7B shows the pressure delivered over a plurality of breathing cycles with a set pressure of 20 cmH2O using a blower of the prior art comprising a Brushless DC motor.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Induction Motor 5.1.1 Motor Construction

Figure 1:
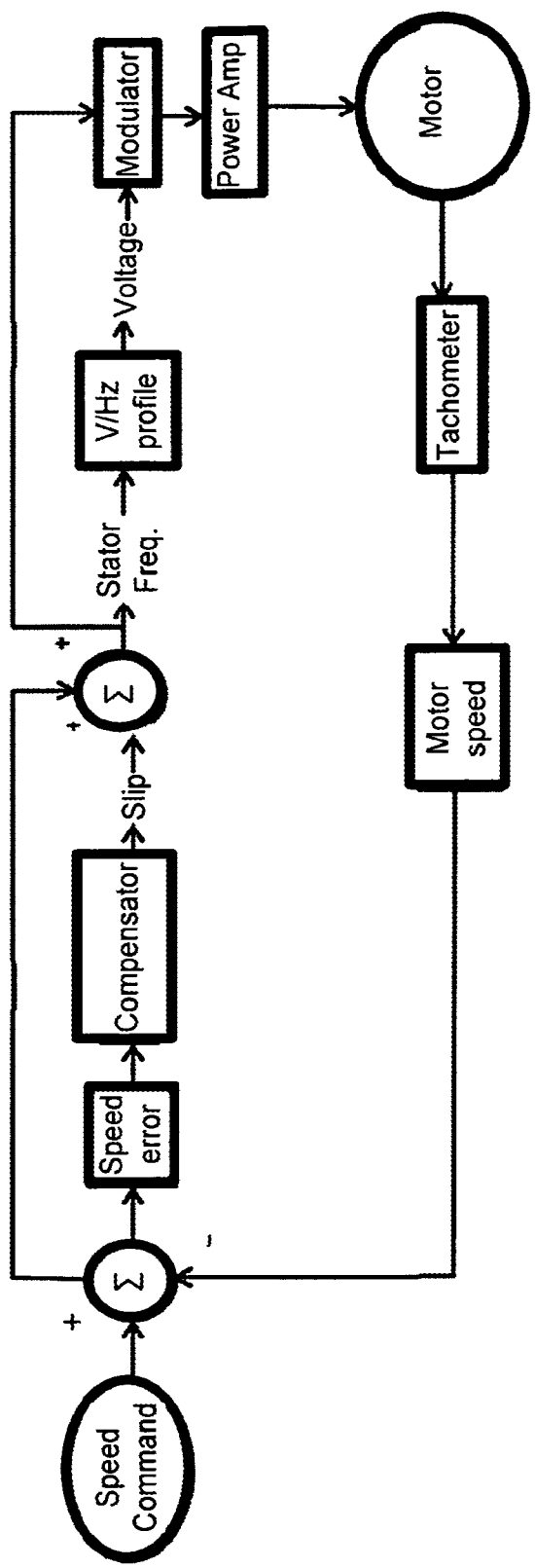
FIG. 1 shows an example block diagram of a prior art control system for an induction motor using a tachometer.
Figure 2A:
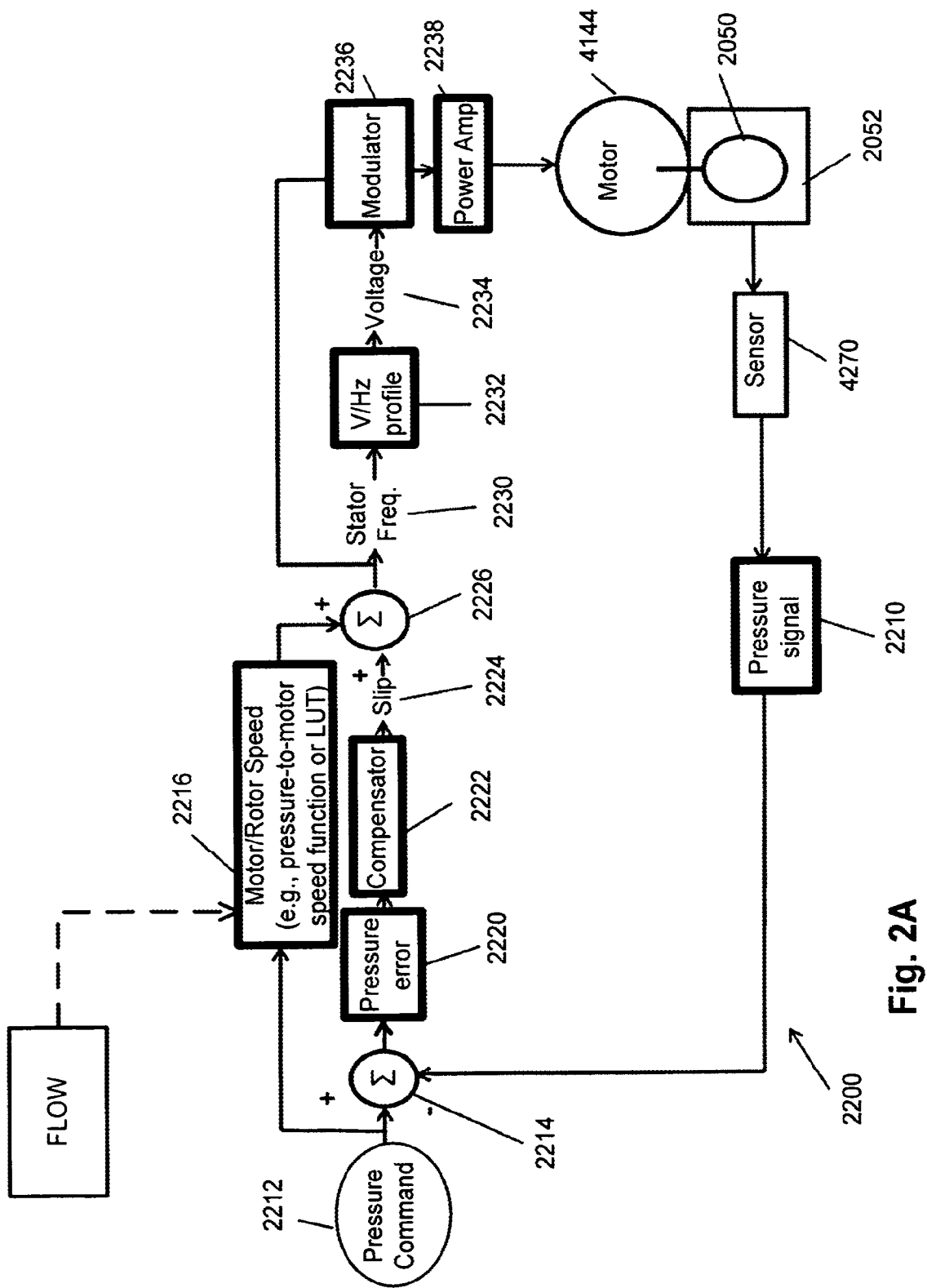
FIG. 2A shows an example block diagram of process elements of a control system for an induction motor in accordance with an aspect of the present technology.
Figures 2B, 2C:
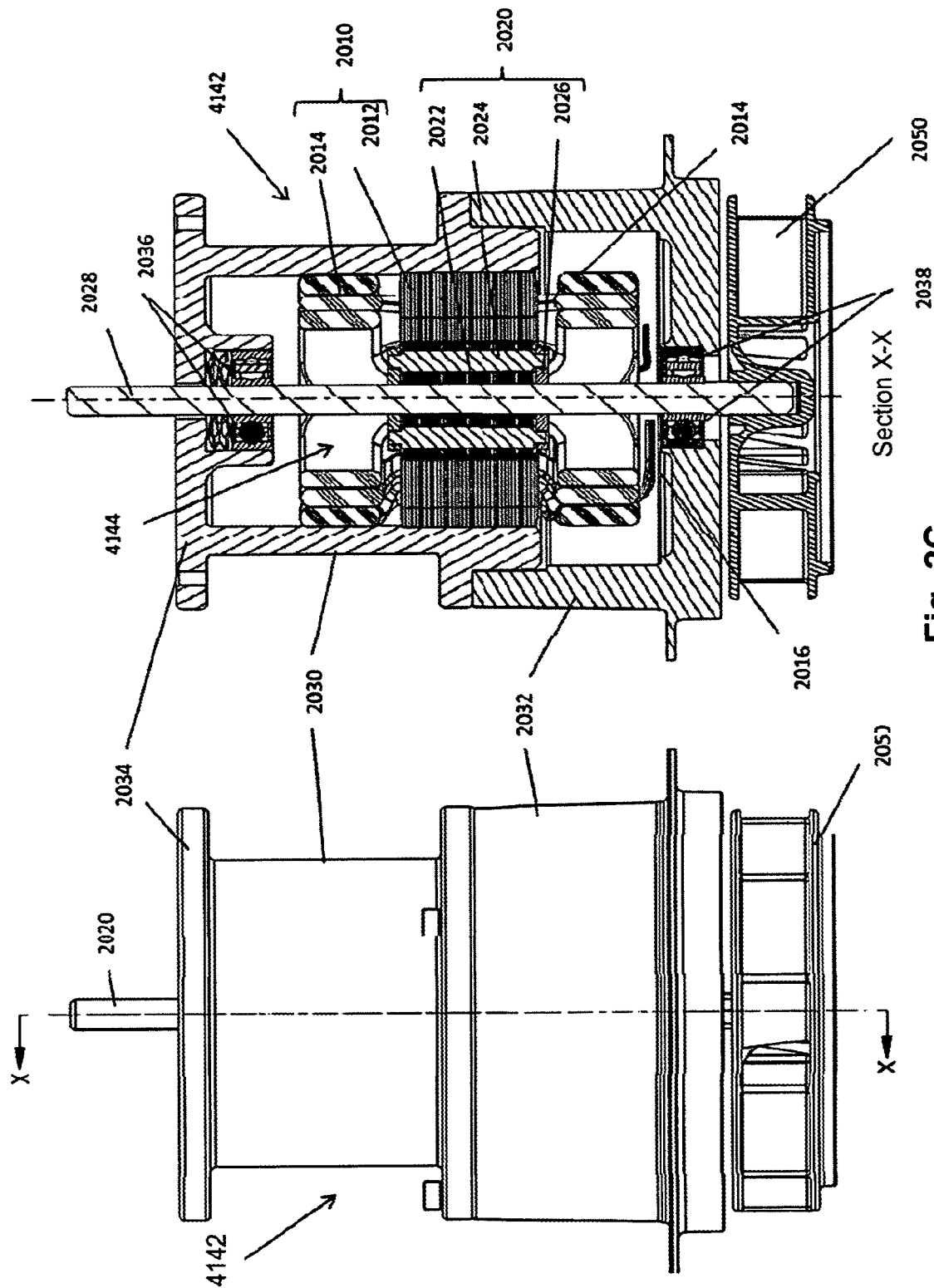
FIG. 2B is a side view of an example blower assembly in some implementations of the present technology.
FIG. 2C is a cross-sectional view through line X-X of the blower assembly in FIG. 2B.

In one form, such as that illustrated in the example of FIGS. 2B and 2C, the present technology comprises an induction motor 4144 including a stator 2010 and a rotor 2020 positioned within the stator 2010. The stator 2010 comprises a lamination stack 2012 of a magnetically conductive material, such as steel, and a plurality of windings 2014 wound around the laminated stack to form a plurality of stator poles. The stator 2010 includes an even number of stator poles such as 4, 6, 8, 10, 12, 16, 20, 24 or more stator poles. The number of stator poles may vary depending upon the size and use of the motor. The winding 2014 are formed from a plurality of wires 2016, such as three wires, wound around the stator poles in a three-phase distributed winding configuration. A rotor 2020 is positioned within the stator 2010. The rotor is preferably a squirrel case rotor. The rotor 2020 comprises a lamination stack 2022 formed of magnetically conductive material, such as steel or stainless steel, including a plurality of slots that are configured to receive a plurality of rotor bars 2024. The rotor bars 2024 are formed of an electrically conductive metal such as copper or iron. Each rotor slot receives one rotor bar and an end ring 2026 is electrically connected to each end of the rotor bars 2024 to form a rotor assembly 2020. Each of the rotor bars and slots form a rotor pole, the number of rotor poles may vary depending upon the size and use of the motor. For example there may be 8, 10, 12, 14, 16, 18, 20, 30 or more rotor poles. A shaft 2028 may be coupled to the rotor 2020 such that the shaft 2028 is rotated with the rotor 2020 and may be considered part of the rotor assembly 2020. At least one impeller 2050 may be coupled to the shaft 2028 and be caused to rotate with the rotating rotor assembly 2020.

FIGS. 2B and 2C shows an example of blower including an induction motor 4144 showing a rotor assembly 2020 positioned within a stator 2010 and an impeller 2050 coupled to an end of a shaft 2028. The rotor assembly 2020 may also include one or more balance rings (not shown). The motor 4144 or the impeller(s) 2050 may be inserted or positioned within a volute (not shown) to form a blower such as the example blower 4142 illustrated in FIG. 4A so that the motor 4144 may serve as part of a blower 4142 of a RPT device 4000. In such an arrangement the impeller 2050 is configured to generate a pressurized flow of gas, such as air.

5.1.2 Motor Control

In one form, the present technology includes a control system performed by a motor controller for controlling the speed of the rotor of an induction motor. Such a control system may be implemented as a controller that may include one or more processors and/or other circuit elements, such as comparators, summers, memory etc. to implement the functions/processes of FIGS. 2A and 2B. The induction motor is preferably in a blower. The control system is an error compensator control system, such as a pressure error compensator control system. An error compensator control system measures a characteristic of the flow of fluid produced by the induction motor based blower and compares the measured characteristic to a pre-set level of the characteristic of the flow of fluid to be produced by the induction motor based blower. The difference or error between the measured characteristic and the pre-set or desired level of the characteristic is used to control the speed of the rotor. For example by adjusting the slip frequency. The slip frequency is used to change the voltage and frequency supplied to the stator. The characteristic of the flow of fluid may include a pressure, flow rate, temperature or other parameter that may be measured based on the flow of fluid produced by the rotating rotor.

One example form of the control system 2200 that uses pressure as the characteristic of the flow of fluid is shown in FIG. 2A. The blower including at least one impeller 2050 attached to the rotor and a volute 2052 is configured to generate a pressurized supply of a fluid, such as a flow of gas. The control system includes a sensor or transducer 4270 configured to provide a signal 2210 indicative of the pressure of the flow of fluid generated by the blower. The sensor 4270 is preferably a pressure sensor 4272 and is located at, near or downstream of the outlet of the blower 4142. A measured pressure signal 2210 is provided to a comparator 2214 (such as a summer) and compared to a set pressure level or pressure command 2212 to determine a pressure error 2220.

The set pressure level or pressure command 2212 is a desired pressure level or a predetermined pressure that may be entered via a user interface by a user such as a patient or clinician or may be determined from a previous titration assessment or based on previous treatment session data or any of the treatment pressure control algorithms described in more detail herein. A desired rotor speed or motor speed is determined, such as in a pressure to speed conversion process element 2216, based on the set pressure or pressure command. It is to be understood that when referring to motor speed it is the speed of the rotor that is being referred to. A pressure to motor speed pre-calibration may be performed for the blower to specify a relationship between the set pressure and the motor speed for the blower. The calibrated relationship data may be saved in a memory of the controller for use by the control system. In one form a look-up table (LUT) of pressure to motor speed data is generated and saved in the memory. The pre-calibration step may be performed on one or more blowers including an induction motor having a specific configuration and saved as a general fan curve look-up table that is then used for all blowers having the same or similar configuration. Alternatively the pre-calibration step may be performed at the time of manufacture or assembly of the blower for each individual blower prior to use. Optionally, the look-up table of pressure to speed conversion process element 2216 may also be based on a desired flow rate setting as illustrated in FIG. 2A (shown as FLOW). Thus, the motor speed determined in element 2216 may be based on a look-up of both pressure and flow.

Upon receiving the pressure command 2212 the control system determines the desired motor or rotor speed at element 2216 as described above. A pressure loop compensator 2222 compensates for the pressure error by determining a slip frequency 2224. The slip frequency 2224 is required to maintain the set pressure by eliminating or minimizing the determined pressure error between the set pressure and a measured pressure. The slip frequency 2224 is then combined with the determined motor speed or frequency from element 2216 to determine the required stator frequency 2230 such as in summer 2226. Based on the required stator frequency 2230 a voltage is determined with a voltage and frequency profile 2232 such as by a conversion function. Voltage and frequency have a linear relationship and may be provided in a form of a look-up table. Thus the required voltage 2234 for the stator is determined and may be provided to a modulator to adjust the level of voltage being provided from a power source to the stator. The modulator 2236 creates, for example, a three-phase reference voltage by combining the amplitude voltage from voltage 2234 and the stator frequency 2230 from summer 2226 and calculating a duty cycle for switching gates at the Power Amp 2238. The Power Amp 2238 provides the required voltage to the motor based on the set duty cycle. This process is repeated in an attempt to minimise the pressure error and consequently control the speed of the rotor to provide the set pressure. Thus, providing a pressure error compensator control system.

In one form of the control system the motor speed from element 2216 is determined and fixed based on the pressure command 2212 and is not adjusted unless the pressure command 2212 is adjusted. It is the stator frequency 2230 that is adjusted in an attempt to reduce the pressure error 2220, for example to reduce the pressure error 2220 to approximately zero.

For example in one form the control system may control the pressure in the following manner. If the pressure signal 2210 (using the sensor 4270) is lower than the pressure command 2212, the pressure error 2220 is determined to be positive and consequently the slip frequency 2224 is increased. The stator frequency 2230 is the summation of the rotor frequency/speed and the slip frequency/speed and is therefore also increased resulting in an increase in the voltage 2234 supplied to the motor and this results in an increase in the pressure produced by the blower in an attempt to reduce the pressure error 2220 to zero or close to zero.

Optionally, a version of the control system described herein, such as FIG. 2A, may be implemented for flow control rather than pressure control. Thus, as illustrated in FIG. 2A, a flow command or flow rate setting (shown as FLOW in FIG. 2A) may be applied to element 2216 where a flow-to-motor speed data look up table may determine the motor speed or frequency. In such a version, the sensor 4270 may be a flow sensor that generates a flow rate signal rather than pressure signal 2210 and no pressure command 2212 may be provided. In the case of the flow command, pressure error 2220 would instead be a flow rate error and the pressure loop compensator 2222 would instead be a flow loop compensator for determining the slip frequency 2224.

In another example, in one form the control system may control the pressure such that when the pressure signal 2210 is higher than the pressure command 2212, the pressure error 2220 is determined to be negative and consequently the slip frequency 2224 will be reduced. The stator frequency 2230 will also be reduced and due to a linear relation between frequency and the voltage in a look-up table, the voltage 2234 will be reduced and the pressure produced by the blower will be decreased in an attempt to reduce the pressure error to zero or close to zero.

Figure 2D:
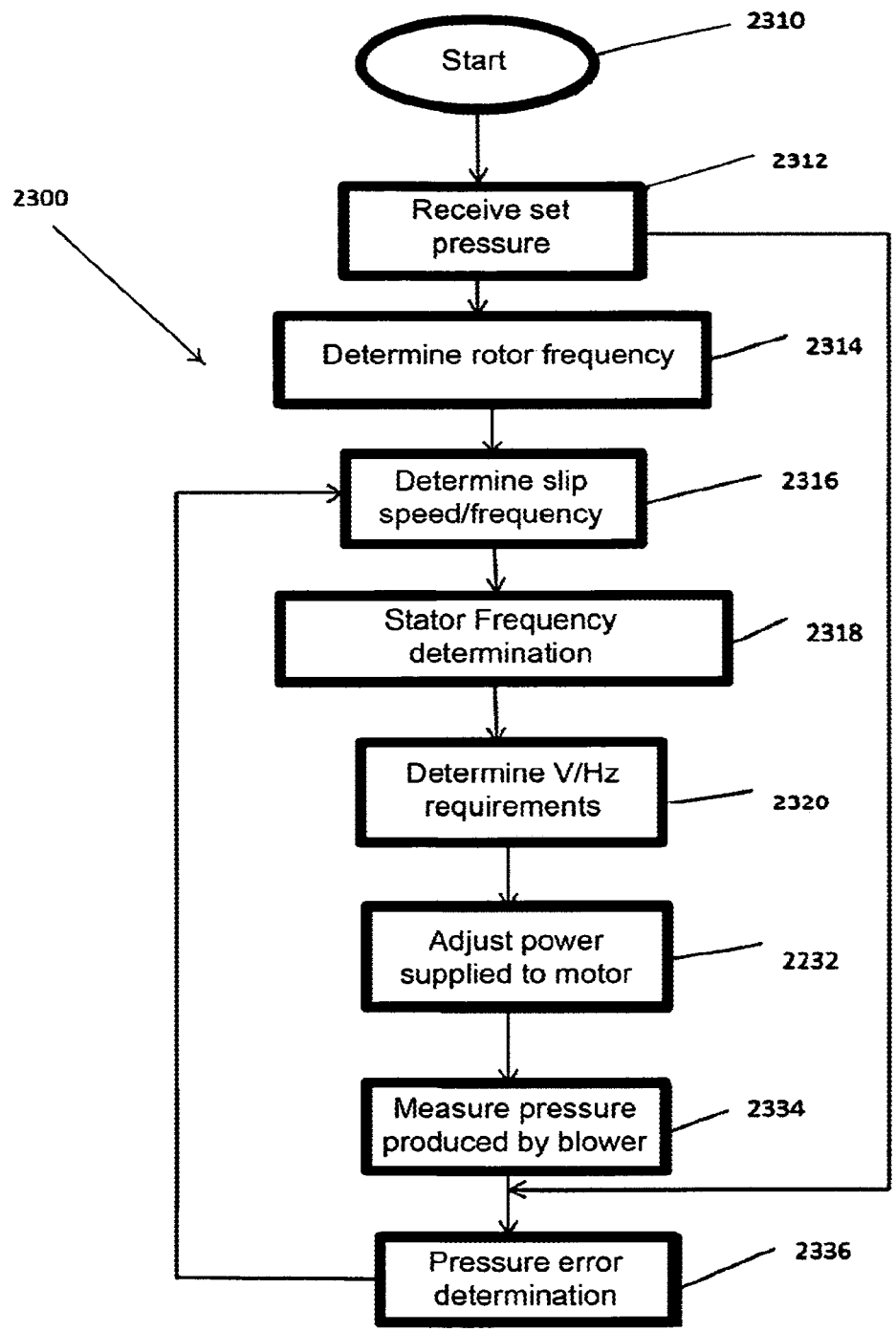
FIG. 2D is a flow chart showing an example process to control the speed of the motor based on a pressure signal.

The methodology of FIG. 2d is an example processing algorithm for a control system 2300 showing the control steps performed by a pressure compensator motor controller to control the speed of the motor or rotor according to a form of the present technology. The controller initially starts 2310 by receiving a set pressure 2312 instruction and then based on the set pressure determines the required rotor frequency 2314. A slip speed/frequency 2316 is initially determined and may be a predefined starting value that is provided from a motor pre-calibration step or a set percentage of the determine rotor frequency such as 1-5%, 2%, 3%, or 4% or some other value. Subsequent determinations of the slip speed/frequency 2316 are determined based on the level of the pressure error. A stator frequency determination 2318 step occur in which the stator frequency is determined as the sum of the slip speed/frequency and the rotor frequency. Based on the linear relationship between voltage and frequency of the stator the voltage required from the power supply is determined in a V/Hz requirement determination step 2320. Based on this determined voltage a power adjustment step 2332 is performed to adjust the power supplied to the motor in accordance with the determined voltage level. This results in the stator rotating at a desired frequency and consequently the rotor of the induction motor to rotate. The rotation of the rotor assembly rotates the impeller 2050 due to the impeller being coupled to the rotor assembly via the shaft. The rotating impeller 2050 produces a flow of fluid, such as gas or air, to flow around the volute and out of the blower. The pressure of the flow of fluid is measured in a pressure measurement step 2334 by the sensor 4270 to provide a measure of the pressure of the fluid. The measured pressure is compared to the set pressure in a pressure error determination step 2336. The pressure error is feedback used to recalculate the slip speed or slip frequency 2316 in an attempt to adjust the pressure error to zero or close to zero. Adjusting the pressure error to zero or close to zero will ensure that rotor or motor speed is rotating at the appropriate speed to provide the set pressure. Any errors in the determination of the set rotor speed or rotor frequency 2316 will be compensated for by the pressure error reduction process.

For a blower 4142 used in a respiratory device a patient breathing on the RPT device 4000 will cause changes in the load on the motor depending upon the breathing cycle which will result in changes in the motor speed and consequently changes in the generated pressure. For example when a patient is inhaling there is a higher load on the motor and this will result in decreases in the pressure. In contrast when a patient is exhaling there is a lower load on the motor and consequently the pressure will increase. Consequently a motor control system is required to maintain the set pressure in response to the changes in load. The pressure will be maintained by identifying changes in the pressure error and compensating for the pressure error by adjusting the slip frequency and ultimately the voltage and frequency supplied to the motor. However, based on the inertia of the system and how responsive the motor controller is a small pressure swing on the pressure may be observed.

In some versions of the present technology, the compensator 2222, may be implemented with a P (proportional), PI (proportional integral) or PID (proportional integral derivative) methodology, such as by determining the integral and/or derivative of the error and applying one or more gains. For example, to adjust the slip frequency variable to control the pressure, a PI methodology may determine the integral of the pressure error 2220. It may then apply (e.g., multiply) a proportional gain to the pressure error. It may apply an integral gain to the result of the integrated error. The computations may then be taken to produce the slip speed/frequency 2224, such as by addition. Thus, the compensator may include one or more gains, such as a constant gain (e.g., a constant proportional gain and/or a constant integration gain.) These gains may be determined by experimental analysis so as to tune these parameters (e.g., in a pre-calibration process) based on the specific motor design. Stability and the dynamic performance may be considered in such a tuning process. The constant parameters can be dependent on the system dynamics like inertia of the motor, inertia of the impeller, the tube impedance and motor geometry. In one example embodiment, the compensator may implement the following output equation:

$$Kp \times \Delta + Ki \int \Delta dt$$

Where $\Delta$ is the pressure error
Kp=proportional gain; and
Ki=integral gain.

5.2 Treatment Systems

In one form, the present technology comprises apparatus for treating a respiratory disorder. The apparatus may comprise a flow generator or blower including an inductance motor for supplying pressurised respiratory gas, such as air, to the patient 1000 via an air circuit 4170 leading to a patient interface 3000.

5.3 Therapy

In one form, the present technology comprises method for treating a respiratory disorder comprising the step of applying positive pressure to the entrance of the airways of a patient 1000 using a pressure generator device 4140 including an induction motor 4144.

5.3.1 CPAP for OSA

In one form, the present technology comprises a method of treating Obstructive Sleep Apnea in a patient by applying continuous positive airway pressure to the patient using a patient interface.

In certain embodiments of the present technology, a supply of air at positive pressure is provided to the nasal passages of the patient via one or both nares.

A patient interface 3000 is provided as seen in FIG. 3 to deliver the supply of pressurized air to the patient's airways. A number of different types of patient interfaces including non-invasive and invasive interfaces are available. For example non-invasive masks include a nasal mask, full face mask, nasal prongs and nasal pillows and invasive interfaces include a tracheostomy tube. Non-invasive patient interfaces 3000 comprise a seal-forming structure to engage with a patient's face in use.

5.4 RPT Device 4000

As shown in FIGS. 4A to 4D a RPT device 4000 in accordance with one aspect of the present technology comprises mechanical and pneumatic components 4100, electrical components 4200 and is programmed to execute one or more algorithms 4300. The RPT device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the RPT device 4000 comprises a chassis 4016 that supports one or more internal components of the RPT device 4000. In one form a pneumatic block 4020 is supported by, or formed as part of the chassis 4016. The RPT device 4000 may optionally include a handle 4018.

The pneumatic path of the RPT device 4000 preferably comprises an inlet air filter 4112, an inlet muffler 4122, a controllable pressure generator device 4140 capable of supplying air at positive pressure (preferably a blower 4142) including a motor 4144, and an outlet muffler 4124. One or more pressure sensors 4272 and flow sensors 4274 are included in the pneumatic path.

The preferred pneumatic block 4020 comprises a portion of the pneumatic path that is located within the external housing 4010.

As seen in FIG. 4C, the RPT device 4000 may include an electrical power supply 4210, a pressure generator 4140, one or more input devices 4220, a central controller 4230, and one or more output devices 4290. Electrical components 4200 may be mounted on a single Printed Circuit Board Assembly (PCBA) 4202. In an alternative form, the RPT device 4000 may include more than one PCBA 4202.

The central controller 4230 of the RPT device 4000 is programmed to execute one or more algorithm modules 4300, preferably including a pre-processing module 4310, a therapy engine module 4320, a therapy control module 4330, and further preferably a fault condition module 4340.

5.4.1 RPT Device Mechanical & Pneumatic Components 4100

A RPT device in accordance with one form of the present technology comprises a range of mechanical and pneumatic components 4100 as illustrated in FIG. 4B. For example the mechanical and pneumatic components 4100 may include combinations of one or more of the following components an air filter 4110, a muffler 4120, a pressure generator device 4140, transducers 4270, anti-spill back valve 4160, air circuit 4170 and supplemental oxygen supply 4180.

In one form the RPT device 4000 may include an air filter 4110, or a plurality of air filters 4110. For example, an inlet air filter 4112 may be located at the beginning of the pneumatic path upstream of a blower 4142. Optionally an outlet air filter 4114, for example an antibacterial filter, may be located between an outlet of the pneumatic block 4020 and a patient interface 3000.

In one form of the present technology, an inlet muffler 4122 may be located in the pneumatic path upstream of a blower 4142. Alternatively or additionally an outlet muffler 4124 may be located in the pneumatic path between the blower 4142 and a patient interface 3000.

In a preferred form of the present technology, a pressure generator device 4140 for producing a flow of air at positive pressure is a controllable blower 4142. For example the blower 4142 may include an induction motor 4144 with one or more impellers housed in a volute. The blower may be preferably capable of delivering a supply of air, for example about 120 litres/minute, at a positive pressure in a range from about 4 $cmH_2O$ to about 20 $cmH_2O$, or in other forms up to about 30 $cmH_2O$.

In one form of the present technology, the RPT device 4000 may include a therapy device controller configured to control the pressure generator device 4140 to deliver pressure and forms part of the algorithms 4300 executed by the central controller or processor 4230.

In one form of the present technology, one or more transducers 4270 are located upstream of the pressure generator device 4140. The one or more transducers 4270 are constructed and arranged to measure properties of the air at that point in the pneumatic path. The one or more transducers 4270 may include flow, pressure, humidity or temperature sensors.

Transducers may be internal of the device, or external of the RPT device. External transducers may be located for example on or form part of the air delivery circuit, e.g. the patient interface. External transducers may be in the form of non-contact sensors such as a Doppler radar movement sensor that transmit or transfer data to the RPT device.

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element. Other flow sensors may also be implemented such as a hot wire flow sensor.

In use, a signal representing total flow Qt from the flow transducer 4274 is received by the central controller 4230.

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the central controller 4230. In one form, the signal from the pressure transducer 4272 is filtered prior to being received by the central controller 4230.

In one form of the present technology, one or more transducers 4270 are located downstream of the pressure generator device 4140, and upstream of the air circuit 4170. The one or more transducers 4270 are constructed and arranged to measure properties of the gas or air at that point in the pneumatic path.

In one form of the present technology, one or more transducers 4270 are located proximate to the patient interface 3000.

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

An air circuit 4170 in accordance with an aspect of the present technology is constructed and arranged to allow a flow of air or breathable gasses between the pneumatic block 4020 and the patient interface 3000.

In one form of the present technology, supplemental oxygen 4180 is delivered to a point in the pneumatic path. The supplemental oxygen 4180 may be delivered upstream of the pneumatic block 4020, to the air circuit 4170 and/or to the patient interface 3000.

5.4.2 RPT Device Electrical Components 4200

The RPT device 4000 comprises a number of electrical components 4200 wherein a power supply 4210 supplies power to the other components of the RPT device 4000 including one or more of an input device 4220, a central controller 4230, the pressure generator device 4140, and output devices 4290.

In one form of the present technology, the power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

A RPT device 4000 may include one or more input devices 4220. Input devices 4220 comprises buttons, switches or dials to allow a person to interact with the RPT device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

In one form of the present technology, the central controller or processor 4230 is a dedicated electronic circuit configured to receive input signal(s) from the input device 4220, and to provide output signal(s) to the output device 4290 and/or the therapy device controller.

In one form, the central controller 4230 is an application-specific integrated circuit. In another form, the central controller 4230 comprises discrete electronic components.

In one form of the present technology, the central controller 4230 is a processor suitable to control a RPT device 4000. Example central controllers 4230 include an x86 INTEL processor; a processor based on ARM Cortex-M processor from ARM Holdings, such as an STM32 series microcontroller from ST MICROELECTRONICS; a member selected from the family ARM9-based 32-bit RISC CPUs, such as an STR9 series microcontroller from ST MICROELECTRONICS; or a 16-bit RISC CPU such as a processor from the MSP430 family of microcontrollers, manufactured by TEXAS INSTRUMENTS; or any other suitable processor or group of processors.

The processor 4230 is configured to receive input signal(s) from one or more transducers 4270, and one or more input devices 4220.

The processor 4230 is configured to provide output signal(s) to one or more of an output device 4290, a therapy device controller, a data communication interface and humidifier controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a RPT device 4000. However, in some forms of the present technology the processor(s) may be implemented discretely from the flow generation components of the RPT device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

Preferably RPT device 4000 includes a clock that is connected to the central controller 4230 and is capable of recording, monitoring or counting time.

In one form of the present technology, the pressure generator device 4140 is configured to deliver therapy to a patient 1000 under the control of the central controller 4230.

Preferably a RPT device 4000 in accordance with the present technology comprises one or more protection circuits such as an electrical protection circuit, a temperature safety circuit or a pressure safety circuit.

In accordance with one form of the present technology the RPT device 4000 includes memory, preferably non-volatile memory. In some forms, memory may include battery powered static RAM. In some forms, memory may include volatile RAM. Preferably memory is located on PCBA 4202. Memory may be in the form of EEPROM, or NAND flash. Additionally or alternatively, RPT device 4000 includes removable form of memory, for example a memory card made in accordance with the Secure Digital (SD) standard.

In one form of the present technology, the memory acts as a non-transitory computer readable storage medium on which is stored computer program instructions expressing the one or more methodologies described herein, such as the one or more algorithms 4300.

In one preferred form of the present technology, a data communication interface is provided, and is connected to processor 4230. Data communication interface is preferably connectable to a remote and/or local external communication network such as the internet. In one form, data communication interface is part of processor 4230. In another form, data communication interface is an integrated circuit that is separate from processor 4230.

The data communication interface may use wired communication (e.g. via Ethernet, or optical fibre) or a wireless protocol to connect to the Internet. The local external communication network may utilise one or more communication standards, such as Bluetooth, or a consumer infrared protocol.

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

A display driver receives as an input the characters, symbols, or images intended for display on the display, and converts them to commands that cause the display to display those characters, symbols, or images.

A display is configured to visually display characters, symbols, or images in response to commands received from the display driver. For example, the display may be an eight-segment display, in which case the display driver converts each character or symbol, such as the figure "0", to eight logical signals indicating whether the eight respective segments are to be activated to display a particular character or symbol.

5.4.3 RPT Device Algorithms 4300

The RPT device 4000 may include a plurality of algorithms 4300 including a number of different modules such as a pre-processing module 4310, a therapy engine module 4320 and a therapy control module 4330.

A pre-processing module 4310 in accordance with the present technology receives as an input, raw data from a transducer 4270, for example a flow or pressure transducer or sensor, and preferably performs one or more process steps to calculate one or more output values that will be used as an input to another module, for example the therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation algorithm 4312, vent flow calculation algorithm 4314, leak flow algorithm 4316 and respiratory flow algorithm 4318.

A pressure compensation algorithm 4312 may receive as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

A vent flow calculation algorithm 4314 may receive as an input an estimated pressure, Pm, in the patient interface 3000 and estimates a vent flow of air, Qv, from a vent 3400 in a patient interface 3000.

A leak flow algorithm 4316 may receive as an input a total flow, Qt, and a vent flow Qv, and provides as an output a leak flow Ql by calculating an average of Qt-Qv over a period sufficiently long to include several breathing cycles, e.g. about 10 seconds.

A respiratory flow algorithm 4318 may receive as an input a total flow, Qt, a vent flow, Qv, and a leak flow, Ql, and estimates a respiratory flow of air, Qr, to the patient, by subtracting the vent flow Qv and the leak flow Ql from the total flow Qt.

In one form of the present technology, a therapy engine module 4320 may receive as inputs one or more of a pressure, Pm, in a patient interface 3000, and a respiratory flow of air to a patient, Qr, and provides as an output, one or more therapy parameters, such as a CPAP treatment pressure Pt, a level of pressure support, and a target ventilation.

In various forms of the present technology, the therapy engine module 4320 comprises one or more of the following algorithms: phase determination 4321, waveform determination 4322, ventilation determination 4323, flow limitation determination 4324, Apnea/hypopnea determination 4325, Snore determination 4326, Patency determination 4327, Target ventilation determination 4328 and Therapy parameter determination 4329.

A phase determination algorithm 4321 may receive as an input a signal indicative of respiratory flow, Qr, and provides as an output a phase of a breathing cycle of a patient 1000. The phase output may be a discrete variable with values of one of inhalation, mid-inspiratory pause, and exhalation. Alternatively the phase output is a continuous variable, for example varying from 0 to 1, or 0 to 2Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

A waveform determination algorithm 4322 may receive as an input a value indicative of current patient ventilation, Vent, and provides as an output a waveform of pressure vs. phase. A ventilation determination algorithm 4323 may receive as an input a respiratory flow Qr, and determines a measure indicative of patient ventilation, Vent. For example the ventilation determination algorithm 4323 may determine a current value of patient ventilation, Vent, as half the low-pass filtered absolute value of respiratory flow, Qr.

A flow limitation determination algorithm 4324 may receive as an input a respiratory flow signal Qr and provides as an output a metric of the extent to which the inspiratory portion of the breath exhibits inspiratory flow limitation.

An Apnea/hypopnea determination algorithm 4325 may receive as an input a respiratory flow signal Qr and provide as an output a flag that indicates that an apnea or an hypopnea has been detected.

An apnea may be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

A hypopnea may be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

A snore determination algorithm 4326 may receive as an input a respiratory flow signal Qr and provides as an output a metric of the extent to which snoring is present. Preferably the snore determination algorithm 4326 comprises the step of determining the intensity of the flow signal in the range of 30-300 Hz. Further preferably, snore determination algorithm 4326 comprises a step of filtering the respiratory flow signal Qr to reduce background noise, e.g. the sound of airflow in the system from the blower. The snore determination algorithm 4326 may comprise comparing the noise generated during inspiration to the noise generated during expiration to determine the occurrence of snore, where the noise generated during expiration is considered to relate to the intrinsic device noise.

In one form an airway patency determination algorithm 4327 may receive as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In another form, an airway patency determination algorithm 4327 may receive as an input a respiratory flow signal Qr, and determines the presence or absence of a cardiogenic signal. The absence of a cardiogenic signal is taken to be an indication of a closed airway.

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi) + P_0$$

where:
A is the pressure support,
$\Pi(\Phi)$ is the waveform template value (in the range 0 to 1) at the current value $\Phi$ of phase, and
$P_0$ is a base pressure By determining the treatment pressure Pt using any suitable equation, the therapy parameter determination algorithm 4329 oscillates the treatment pressure Pt in synchrony with the spontaneous respiratory effort of the patient 1000. That is to say, based on the typical waveform templates $\Pi(\Phi)$ described above, the therapy parameter determination algorithm 4329 increases the treatment pressure Pt at the start of, or during inspiration and decreases the treatment pressure Pt at the start of, or during expiration. The (non-negative) pressure support A is the amplitude of the oscillation.

If the waveform determination algorithm 4322 provides the waveform template $\Pi(\Phi)$ as a lookup table, the therapy parameter determination algorithm 4329 applies the above equation by locating the nearest lookup table entry to the current value $\Phi$ of phase returned by the phase determination algorithm 4321, or by interpolation between the two entries straddling the current value $\Phi$ of phase.

The values of the pressure support A and the base pressure $P_0$ may be set by the therapy parameter determination algorithm 4329 depending on the chosen pressure therapy mode in the manner described below.

A therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt In one form of the present technology, a processor executes one or more methods for the detection of fault conditions serving as a fault condition module 4340. Preferably the fault conditions detected by the one or more methods includes at least one of the following:

Power failure (no power, or insufficient power)
Transducer fault detection
Failure to detect the presence of a component
Operating parameters outside recommended ranges (e.g. pressure, flow, temperature, PaO$_2$)
Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm
Sending a message to an external device
Logging of the incident

5.5 Humidifier 5000

5.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air from the RPT device 4000, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

According to one arrangement, the humidifier 5000 may comprise a water reservoir 5110 configured to hold, or retain, a volume of liquid (e.g. water) to be used for humidification of the flow of air. The water reservoir 5110 is configured to hold a predetermined maximum volume of water in order to provide adequate humidification for at least the duration of respiratory therapy, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the reservoir dock 5130.

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

The humidifier 5000 may comprise a number of electrical and/or thermal components such as humidifier transducers or sensors 5210, heating element 5240 and humidifier controller 5250.

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

One or more pressure transducers or sensors 5212 may be provided to the humidifier 5000 in addition to, or instead of, a pressure transducer or sensor 4272 provided in the RPT device 4000.

One or more flow rate transducers 5214 may be provided to the humidifier 5000 in addition to, or instead of, a flow rate transducer 4274 provided in the RPT device 4000.

The humidifier 5000 may comprise one or more temperature transducers or sensors 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot, is about 40%.

FIG. 6B shows an example set of flow data for a breathing cycle at a rate of 15 breaths per minute using an IngMar Medical ASL 5000 breathing simulator.

A blower 4142 comprising an induction motor under the control of a pressure compensator control system as described above and shown in FIG. 2A was tested using a breathing machine and the generated pressure measured. The pressure generated over a breathing cycle with a set pressure (e.g., command pressure) of 10 cmH$_2$O such as for a CPAP treatment is illustrated in FIG. 6C. The pressure data illustrates that the induction motor can be controlled via a pressure sensor to maintain a desired pressure profile over a breathing cycle. A pressure swing or difference between peak inspiration and expiration of approximately 1 cm H$_2$O is observed. As the pressure changes due to the changes in load with inspiration and expiration the pressure error compensation control system is able to respond and adjust the delivered pressure to maintain a delivered pressure close to the set pressure.

In comparison, FIG. 6D shows pressure profile data from a test using a brushless DC motor and prior art motor control system with a set pressure of 10 cmH$_2$O. The pressure swing or difference observed with the brushless DC motor is higher at approximately 2 cmH$_2$O.

FIGS. 7A and 7B show further comparison of a pressure profile over a breathing cycle with a set pressure of 20 cmH2O of a blower including an induction motor and a brushless DC motor respectively. The blower including the induction motor and controlled via a pressure error compensation control system as illustrated in FIG. 7A is able to adjust the speed of the motor to maintain a delivered pressure close to the set pressure with the changing loads resulting from inspiration and expiration phases of the breathing cycle. The pressure swing is approximately 2 cmH$_2$O and may be well within any applicable regulatory requirements. The pressure swings using the brushless DC motor (see FIG. 7B) is again slightly larger than those produced using the induction motor pressure error compensation control system.

Thus, a blower including an induction motor may control the speed of the rotor or motor using a pressure error compensator control system according to the present technology. Reducing the cost of controlling the speed of an induction motor and the size of the motor.

5.7 Glossary

For the purposes of the present technology disclosure, in certain forms of the present technology, one or more of the following definitions may apply. In other forms of the present technology, alternative definitions may apply.

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP) therapy: CPAP therapy will be taken to mean the application of a supply of air to the entrance to the airways in which the treatment pressure or set pressure is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is continually automatically adjustable, e.g. from breath to breath, between minimum and maximum limits, depending on the presence or absence of indications of SDB events.

Therapy: Therapy in the present context may be one or more of positive pressure therapy, oxygen therapy, carbon dioxide therapy, control of dead space, and the administration of a drug.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$)

sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Patency (airway): The degree of the airway being open, or the extent to which the airway is open. A patent airway is open. Airway patency may be quantified, for example with a value of one (1) being patent, and a value of zero (0), being closed.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the RPT device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

5.8 Other Remarks

A portion of the disclosure of this patent document contains material which is subject to copyright protection. The copyright owner has no objection to the facsimile reproduction by anyone of the patent document or the patent disclosure, as it appears in the Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The present technology may be considered in relation to the following additional examples:

EXAMPLE 1. A control system for an induction motor configured to adjust a slip frequency of the induction motor based on a measured characteristic of a flow of fluid produced by a rotating rotor of the induction motor.

EXAMPLE 2. The control system of EXAMPLE 1, wherein an impeller is attached to the rotating rotor and configured to rotate with the rotor to produce the flow of fluid.

EXAMPLE 3. The control system of any one of EXAMPLEs 1-2, wherein a rotor speed is predetermined based on a set level of the characteristic of the flow of fluid to be produced by the rotating rotor.

EXAMPLE 4. The control system of any one of EXAMPLEs 1-3, wherein the measured characteristic of the flow of fluid produced by the rotating rotor is compared to a set level of the characteristic of the flow of fluid to be produced by the rotating rotor to determine an error, and wherein the slip frequency is adjusted based on the error.

EXAMPLE 5. The control system of EXAMPLE 4, wherein the slip frequency is adjusted to minimize or eliminate the error.

EXAMPLE 6. The control system of any one of EXAMPLEs 1-5 wherein a stator frequency is adjusted based on the slip frequency.

EXAMPLE 7. The control system of claim 6, wherein the stator frequency is adjusted by adjusting a level of a frequency and voltage supplied to the stator.

EXAMPLE 8. The control system of any one of EXAMPLEs 1-7, wherein the measured characteristic is a pressure of the flow of fluid.

EXAMPLE 9. The control system of EXAMPLE 8, wherein the pressure is measured using a pressure sensor configured at the flow of fluid produced by the rotating rotor.

EXAMPLE 10. The control system of any one of EXAMPLEs 1-7, wherein the measured characteristic is a flow rate of the flow of fluid.

EXAMPLE 11. The control system of EXAMPLE 10 wherein the flow rate is measured using a flow rate sensor configured at the flow of fluid produced by the rotating rotor.

EXAMPLE 12. A control system for an induction motor in a blower, the blower comprising at least one impeller coupled to a rotor of the induction motor and configured to generate a supply of pressurized fluid, the control system comprising a sensor to provide a signal indicative of a measure of a characteristic of the pressurized fluid generated by the blower; and a controller configured to receive the signal and determine the measure of the characteristic of the pressurized fluid being generated, the controller configured to compare the determined measured characteristic with a predetermined level of the characteristic and to adjust a slip frequency of the induction motor as a function of the comparison.

EXAMPLE 13. The control system according to EXAMPLE 12, further comprising adjusting a frequency and voltage supplied to a stator of the induction motor based on the adjusted slip frequency.

EXAMPLE 14. The control system of any one of EXAMPLEs 12-13, wherein the controller compares the determined measure of the characteristic of the pressurized fluid with the predetermined level of the characteristic of the pressurized fluid to determine an error.

EXAMPLE 15. The control system of EXAMPLE 14, wherein the controller adjusts the slip frequency as a function of the error.

EXAMPLE 16. The control system of any one of EXAMPLEs 13-15, wherein the frequency and voltage supplied to the stator is determined as a function of the slip frequency and a set rotor frequency.

EXAMPLE 17. The control system of EXAMPLE 16, wherein a desired rotor speed of the induction motor is determined as a function of the predetermined level of the characteristic.

EXAMPLE 18. The control system of EXAMPLE 17, wherein the desired rotor speed is determined from a look-up table that is stored in a memory of the controller.

EXAMPLE 19. The control system of any one of EXAMPLEs 13-18, wherein if the measured characteristic is greater than the predetermined level of the characteristic a frequency and voltage supplied to the stator is reduced.

EXAMPLE 20. The control system of any one of EXAMPLEs 13-18, wherein if the measured characteristic is less than the predetermined level of the characteristic a frequency and voltage supplied to the stator is increased.

EXAMPLE 21. The control system of any one of EXAMPLEs 12-20, wherein the characteristic of the pressurized fluid generated by the blower is a pressure of the fluid.

EXAMPLE 22. The control system of any one of EXAMPLEs 12-20, wherein the characteristic of the pressurized fluid generated by the blower is a flow rate of the fluid.

EXAMPLE 23. A blower including an induction motor controlled by the control system of any one of claims 12-22.

EXAMPLE 24. A respiratory therapy device comprising the blower according to claim 23.

EXAMPLE 25. A method of controlling a rotor speed of an induction motor by determining a slip frequency based on a measured characteristic of a flow of fluid produced by a rotating rotor of the induction motor and adjusting a stator frequency as a function of the determined slip frequency.

EXAMPLE 26. The method according to EXAMPLE 25 wherein the slip frequency is determined as a function of a difference between the measured characteristic of the flow of fluid produced by the rotating rotor and a pre-set level of the characteristic of the flow of fluid to be produced by the rotating rotor.

EXAMPLE 27. The method according to any one of EXAMPLEs 25-26 wherein the characteristic of the flow of fluid is a pressure of the flow of fluid.

EXAMPLE 28. The method according to any one of EXAMPLEs 25-26 wherein the characteristic of the flow of fluid is a flow rate of the flow of fluid.

EXAMPLE 29. A method of controlling a speed of an induction motor in a blower configured to provide a supply of pressurized fluid, the method comprising:

setting a desired pressure level of the supply of fluid to be provided by the blower;

determining a desired rotor speed based on the set pressure level;

determining a slip frequency and stator frequency based on the desired rotor speed;

providing frequency and voltage to the stator based on the determined stator frequency to induce rotation of the rotor;

measuring a pressure of the pressurized supply of fluid generated by the blower;

comparing the measured pressure and the set pressure to determine a pressure error; and adjusting the slip frequency based on the determined pressure error to minimise the pressure error and adjust the rotor speed of the blower.

5.9 Reference Signs List

| | |
|---|---|
| patient | 1000 |
| bed partner | 1100 |
| stator | 2010 |
| lamination stack | 2012 |
| winding | 2014 |
| wire | 2016 |
| rotor or rotor assembly | 2020 |
| lamination stack | 2022 |
| rotor bar | 2024 |
| end ring | 2026 |
| shaft | 2028 |
| impeller | 2050 |
| volute | 2052 |
| signal or pressure signal | 2210 |
| pressure command or set pressure | 2212 |
| comparator | 2214 |
| motor speed or motor frequency process element | 2216 |
| pressure error | 2220 |
| pressure loop compensator | 2222 |
| slip or slip frequency | 2224 |
| stator frequency | 2230 |
| motor frequency profile | 2232 |
| voltage | 2234 |
| modulator | 2236 |
| current power ampere | 2238 |
| Start step | 2310 |
| receive set pressure | 2312 |
| determine rotor frequency | 2314 |
| determine slip speed/frequency | 2316 |
| stator frequency determination | 2318 |
| Determine V/HZ requirements step | 2320 |
| pressure measurement step | 2334 |
| pressure error determination step | 2336 |
| patient interface | 3000 |
| vent | 3400 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator device | 4140 |
| blower | 4142 |
| motor or induction motor | 4144 |
| back valve | 4160 |
| air delivery tube | 4170 |
| heated air circuit | 4171 |
| supplemental oxygen | 4180 |
| electrical component | 4200 |
| Printed Circuit Board Assembly (PCBA) | 4202 |
| power supply | 4210 |
| input device | 4220 |
| central controller or processor | 4230 |
| memory | 4260 |
| sensor or transducer | 4270 |
| pressure transducer or pressure sensor | 4272 |
| flow rate transducer or flow sensor | 4274 |
| output device | 4290 |
| algorithm | 4300 |
| processing module | 4310 |
| pressure compensation algorithm | 4312 |
| vent flow calculation algorithm | 4314 |
| leak flow algorithm | 4316 |
| respiratory flow algorithm | 4318 |
| therapy engine module | 4320 |
| phase determination algorithm | 4321 |
| waveform determination algorithm | 4322 |

-continued

| | |
|---|---|
| ventilation determination algorithm | 4323 |
| flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| fault condition module | 4340 |
| humidifier | 5000 |
| humidifier inlet | 5002 |
| humidifier outlet | 5004 |
| humidifier base | 5006 |
| reservoir | 5110 |
| conductive portion | 5120 |
| reservoir dock | 5130 |
| locking lever | 5135 |
| water level indicator | 5150 |
| humidifier transducers or sensors | 5210 |
| pressure transducer or sensor | 5212 |
| flow rate transducer | 5214 |
| temperature sensor or transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |

The invention claimed is:

1. A device comprising:
an impeller configured to produce a flow at a positive pressure, and an induction motor including a rotor, wherein the impeller is coupled to the rotor via a shaft; and
a control system for the induction motor configured to adjust a slip frequency of the induction motor based on a measured characteristic of the flow produced by operation of the rotor with the impeller,
wherein the measured characteristic of the flow produced by operation of the rotor with the impeller is compared to a set level of the characteristic of the flow to be produced by operation of the rotor with the impeller to determine an error, and wherein the slip frequency is adjusted based on the error.

2. The device of claim 1, wherein the impeller is configured to rotate with the rotor to produce the flow.

3. The device of claim 1, wherein speed of the rotor is predetermined based on a set level of the characteristic of the flow to be produced by operation of the rotor with the impeller.

4. The device of claim 1, wherein the slip frequency is adjusted to minimize or eliminate the error.

5. The device of claim 1 wherein a stator frequency is adjusted based on the slip frequency.

6. The device of claim 5, wherein the stator frequency is adjusted by adjusting a level of a frequency and voltage supplied to a stator.

7. The device of claim 1, wherein the measured characteristic is a pressure of the flow.

8. The device of claim 7, wherein the pressure is measured using a pressure sensor configured at the flow produced by operation of the rotor with the impeller.

9. The device of claim 1, wherein the measured characteristic is a flow rate of the flow.

10. The device of claim 9 wherein the flow rate is measured using a flow rate sensor configured at the flow produced by operation of the rotor with the impeller.

11. The device of claim 1, wherein the error is input to a compensator that determines the slip frequency from the error.

12. A device comprising:
an impeller configured to produce a flow of positively pressurized fluid, and an induction motor including a rotor, wherein the impeller is coupled to the rotor via a shaft;
a sensor to provide a signal indicative of a measure of a characteristic of the pressurized fluid generated by the impeller; and
a controller configured to receive the signal and determine the measure of the characteristic of the pressurized fluid being generated, the controller configured to compare the determined measured characteristic with a predetermined level of the characteristic and to adjust a slip frequency of the induction motor as a function of the comparison.

13. The device according to claim 12, further comprising adjusting a frequency and voltage supplied to a stator of the induction motor based on the adjusted slip frequency.

14. The device of claim 12, wherein the controller compares the determined measure of the characteristic of the pressurized fluid with the predetermined level of the characteristic of the pressurized fluid to determine an error.

15. The device of claim 14, wherein the controller adjusts the slip frequency as a function of the error.

16. The device of claim 13, wherein the frequency and voltage supplied to the stator is determined as a function of the slip frequency and a set rotor frequency.

17. The device of claim 16, wherein a desired rotor speed of the induction motor is determined as a function of the predetermined level of the characteristic.

18. The device of claim 17, wherein the desired rotor speed is determined from a look-up table that is stored in a memory of the controller.

19. The device of claim 13, wherein if the measured characteristic is greater than the predetermined level of the characteristic a frequency and voltage supplied to the stator is reduced.

20. The device of claim 13, wherein if the measured characteristic is less than the predetermined level of the characteristic a frequency and voltage supplied to the stator is increased.

21. The device of claim 12, wherein the characteristic of the pressurized fluid generated by the impeller is a pressure of the fluid.

22. The device of claim 12, wherein the characteristic of the pressurized fluid generated by the impeller is a flow rate of the fluid.

23. The device according to claim 12, wherein the comparison produces an error, and wherein the error is input to a compensator that determines the slip frequency from the error.

24. A method of controlling a rotor speed of an induction motor in a device by determining a slip frequency based on a measured characteristic of a flow of fluid produced by a rotor of the induction motor and adjusting a stator frequency as a function of the determined slip frequency, wherein the slip frequency is determined as a function of a difference between the measured characteristic of the flow of fluid produced by the rotor and a pre-set level of the characteristic of the flow of fluid to be produced by the rotor.

25. The method according to claim 24 wherein the characteristic of the flow of fluid is a pressure of the flow of fluid.

26. The method according to claim 24 wherein the characteristic of the flow of fluid is a flow rate of the flow of fluid.

27. A method of controlling a speed of an induction motor in a device configured to provide a supply of pressurized fluid, the method comprising:
    setting a desired pressure level of the supply of fluid to be provided by the device;
    determining a desired rotor speed based on the set pressure level;
    determining a slip frequency and stator frequency based on the desired rotor speed;
    providing frequency and voltage to the stator based on the determined stator frequency to induce rotation of the rotor;
    measuring a pressure of the pressurized supply of fluid generated by the device;
    comparing the measured pressure and the set pressure to determine a pressure error; and
    adjusting the slip frequency based on the determined pressure error to minimize the pressure error and adjust the rotor speed of the device.

28. A method of controlling a rotor speed of an induction motor by determining a slip frequency based on a measured characteristic of a flow of fluid produced by operation of a rotor of the induction motor and adjusting a stator frequency as a function of the determined slip frequency, wherein the measured characteristic of the flow of fluid produced by operation of the rotor is compared to a set level of the characteristic of the flow of fluid to be produced by operation of the rotor to determine an error, and wherein the error is input to a compensator that determines the slip frequency from the error.

* * * * *